United States Patent
Ju et al.

(10) Patent No.: US 12,284,986 B2
(45) Date of Patent: Apr. 29, 2025

(54) USE OF MOUSE MODEL IN EVALUATION OF INTELLIGENCE LEVEL

(71) Applicant: GEMPHARMATECH CO., LTD., Nanjing (CN)

(72) Inventors: Cunxiang Ju, Nanjing (CN); Jing Zhao, Nanjing (CN); Jingjing Wang, Nanjing (CN); Zhong Chen, Nanjing (CN)

(73) Assignee: GEMPHARMATECH CO., LTD., Nanjing (CN)

( * ) Notice: Subject to any disclaimer, the term of this patent is extended or adjusted under 35 U.S.C. 154(b) by 0 days.

(21) Appl. No.: 17/427,449

(22) PCT Filed: Sep. 17, 2020

(86) PCT No.: PCT/CN2020/115844
§ 371 (c)(1),
(2) Date: Jul. 30, 2021

(87) PCT Pub. No.: WO2022/027798
PCT Pub. Date: Feb. 10, 2022

(65) Prior Publication Data
US 2023/0148569 A1 May 18, 2023

(30) Foreign Application Priority Data
Aug. 3, 2020 (CN) .......................... 202010764676.3

(51) Int. Cl.
*A01K 29/00* (2006.01)
*A01K 67/02* (2006.01)

(52) U.S. Cl.
CPC ............ *A01K 29/005* (2013.01); *A01K 67/02* (2013.01); *A01K 2227/105* (2013.01); *A01K 2267/03* (2013.01)

(58) Field of Classification Search
CPC .................. A01K 29/005; A01K 67/02; A01K 2227/105; A01K 2267/03
See application file for complete search history.

(56) References Cited

FOREIGN PATENT DOCUMENTS

| CN | 104450602 A | 3/2015 |
| CN | 107771740 A | 3/2018 |
| CN | 110679548 A | 1/2020 |
| WO | 2019145957 A1 | 8/2019 |

OTHER PUBLICATIONS

Xu (G3 Genes|Genomes|Genetics, vol. 6, Issue 11, Nov. 1, 2016, pp. 3571-3580).*
Li (Metabolites, 2022, 121276, p. 1-23).*
Tanila (Behavioral Brain Research, 2018, 3352:23-27).*
Gould, T.D., Dao, D.T., Kovacsics, C.E. (2009). The Open Field Test. In: Gould, T. (eds) Mood and Anxiety Related Phenotypes in Mice. Neuromethods, vol. 42. Humana Press, Totowa, NJ.*
Kraeuter, AK., Guest, P.C., Sarnyai, Z. (2019). The Y-Maze for Assessment of Spatial Working and Reference Memory in Mice. In: Guest, P. (eds) Pre-Clinical Models. Methods in Molecular Biology, vol. 1916. Humana Press, New York, NY. https://doi.org/10.1007/978-1-4939-8994-2_10.*
Xu (Front. Genet., Jan. 9, 2020, 10:11 pages.*
Andreadou (Br J Pharmacol. Jan. 2020;177:5287-5311.*
Vorhees (Nature Protocols | vol. 1 No. 2 | 2006 | 848-858).*
Notice of Grant issued on Dec. 9, 2020 in Patent Application No. 202010764676.3 filed on Aug. 3, 2020 (with English translation), 4 pages.
The 1st Office Action issued on Sep. 16, 2020 in Patent Application No. 202010764676.3 filed on Aug. 3, 2020 (with English translation), 12 pages.
The 2nd Office Action issued on Oct. 12, 2020 in Patent Application No. 202010764676.3 filed on Aug. 3, 2020 (with English translation), 15 pages.
The 3rd Office Action issued on Nov. 2, 2020 in Patent Application No. 202010764676.3 filed on Aug. 3, 2020 (with English translation), 5 pages.
Matzel, L. D. et al., "Individual Differences in the Expression of a "General" Learning Ability in Mice," The Journal of Neuroscience, vol. 23, No. 16, 2003, pp. 6423-6433.
Gao, Chuan, Data Collection and Initial Establishment of Wild Mouse Derived Chromosome 1 Substitution Strain's Database, Chinese Master's Theses Full-text Database, 2015, 60 pages, Abstract only, In chinese.
Michael J. Galsworthy et al., Assessing Reliability, Heritability and General Cognitive Ability in a Battery of Cognitive Tasks for Laboratory Mice, Behavior Genetics, 35(5): 675-692, 2005.
Stefan Kolata et al., Variations in working memory capacity predict individual differences in general learning abilities among genetically diverse mice, Neurobiology of Learning and Memory, 84: 241-246, 2005.
Chinese Association for Laboratory Animal Sciences, Report on Advances in Laboratory Animal Science 2014-2015, China Science and Technology Press, 2016, 7 pages.
Liu, Libing et al., Experimental animal Behavior Methods, Basic Experimental Medicine, 3rd Edition, 2009, 11 pages.
International Search Report in PCT/CN2020/115844 mailed on Apr. 29, 2021, 8 pages.
Written Opinion in PCT/CN2020/115844 mailed on Apr. 29, 2021, 7 pages.

* cited by examiner

*Primary Examiner* — Valarie E Bertoglio
(74) *Attorney, Agent, or Firm* — METIS IP LLC

(57) ABSTRACT

A mouse model may be used in evaluation of the change in intelligence level. The mouse model may be a mouse model with high intelligence level. The mouse chromosome of the mouse model with high intelligence level at least includes all or a portion of chromosome 1 originated from wild-type mouse. The evaluation includes performing a test which may be an open field test, sucrose preference test, water maze test, space exploration Y maze test, active avoidance Y maze test, and/or fatigue rotarod test.

5 Claims, 10 Drawing Sheets

USE OF MOUSE MODEL IN EVALUATION OF INTELLIGENCE LEVEL

CROSS-REFERENCE TO RELATED APPLICATIONS

The present application is the national stage of international application PCT/CN2020/115844, filed on Sep. 17, 2020, and claims the benefit of the filing date of Chinese Appl. No. 202010764676.3, filed on Aug. 3, 2020.

TECHNICAL FIELD

The present application relates to the biomedical field, in particular to use of a mouse model in evaluating the intelligence level.

BACKGROUND OF THE INVENTION

Alzheimer's disease (AD, also known as aged dementia) experimental animal models are important tools for studying the pathogenesis, early diagnosis and drug therapy of the disease, and the scientificity, accuracy and diversity will be important factors to reduce clinical failures of phase III drugs. It is the starting point of Alzheimer's disease experimental animal model research to introduce the Alzheimer's disease associated mutant genes into an animal gene system to simulate these pathological characteristics and behavioral changes of Alzheimer's disease.

However, the aforementioned models are late onset, and false positive or false negative results are prone to occur in the preclinical efficacy test, which is contrary to the characteristics of Alzheimer's disease that the disease involves complex phenotypes and is affected by multiple genes, environment, age, or the like. At present, no suitable animal resource has been found as research tools, which is the sore point of new drug research and development for Alzheimer's disease.

SUMMARY OF THE INVENTION

The present application provides use of a mouse model in evaluation of intelligence level. The mouse model with high intelligence level of the present application can have at least one beneficial effect selected from the group consisting of: 1) having a good learning ability; 2) having a good memory ability; 3) having genetic diversity; 4) being conducive to screening and/or preparing a drug for treating intelligence level associated diseases (e.g., Alzheimer's disease); 5) being conducive to increasing the safety and/or efficacy of drugs and/or therapeutic regimens for treating intelligence level associated diseases (e.g., Alzheimer's disease); and 6) being conducive to comprehensively analyzing the molecular mechanism of intelligence level associated disease.

In an aspect, the present application provides use of a mouse model in evaluation of a change in intelligence level, wherein the mouse model is a mouse model with high intelligence level; the mouse chromosome of the mouse model with high intelligence level at least includes all or a portion of chromosome 1 originated from wild-type mouse; and the evaluation include performing a test selected from the group consisting of open field test, sucrose preference test, water maze test, space exploration Y maze test, active avoidance Y maze test, and fatigue rotarod test.

In some embodiments, the mouse is originated from Strain C57BL/6J.

In some embodiments, the intelligence level is determined by evaluating one or more conditions selected from the group consisting of motor ability, emotional state, learning ability, memory ability and space exploration ability.

In some embodiments, the motor ability is evaluated by the open field test.

In some embodiments, the emotional state is evaluated by the sucrose preference test.

In some embodiments, the learning ability and/or the memory ability are/is evaluated by the water maze test.

In some embodiments, the memory ability and/or the space exploration ability are/is evaluated by the space exploration Y maze test.

In some embodiments, the memory ability is evaluated by the active avoidance Y maze test.

In some embodiments, the motor ability is evaluated by the fatigue rotarod test.

In another aspect, the present application provides a system including a mouse model with high intelligence level; wherein the mouse chromosome of the mouse model with high intelligence level at least includes all or a portion of chromosome 1 originated from wild-type mouse; the system further includes an identification module for evaluating a change in intelligence level of mouse in the mouse model with high intelligence level; and the identification module includes reagent(s) and/or instrument(s) for performing a test selected from the group consisting of open field test, sucrose preference test, water maze test, space exploration Y maze test, active avoidance Y maze test, and fatigue rotarod test.

Persons skilled in the art can easily recognize other aspects and advantages of the present application from the following detailed description. The following detailed description only shows and describes exemplary embodiments of the present application. As persons skilled in the art will appreciate, the present application enables persons skilled in the art to make modifications to the disclosed embodiments without departing the spirit and scope of the invention involved in the present application. Correspondingly, the accompanying drawings and description in the specification of the present application are only illustrative, rather than restrictive.

BRIEF DESCRIPTION OF THE DRAWING

The specific features of the invention involved in the present application are shown in the appended claims. By referring to the exemplary embodiments as detailedly described below and the accompanying drawings, the features and advantages of the invention involved in the present application can be better understood. The accompany drawings are briefly described as follows:

DETAILED DESCRIPTION

Figure 1:
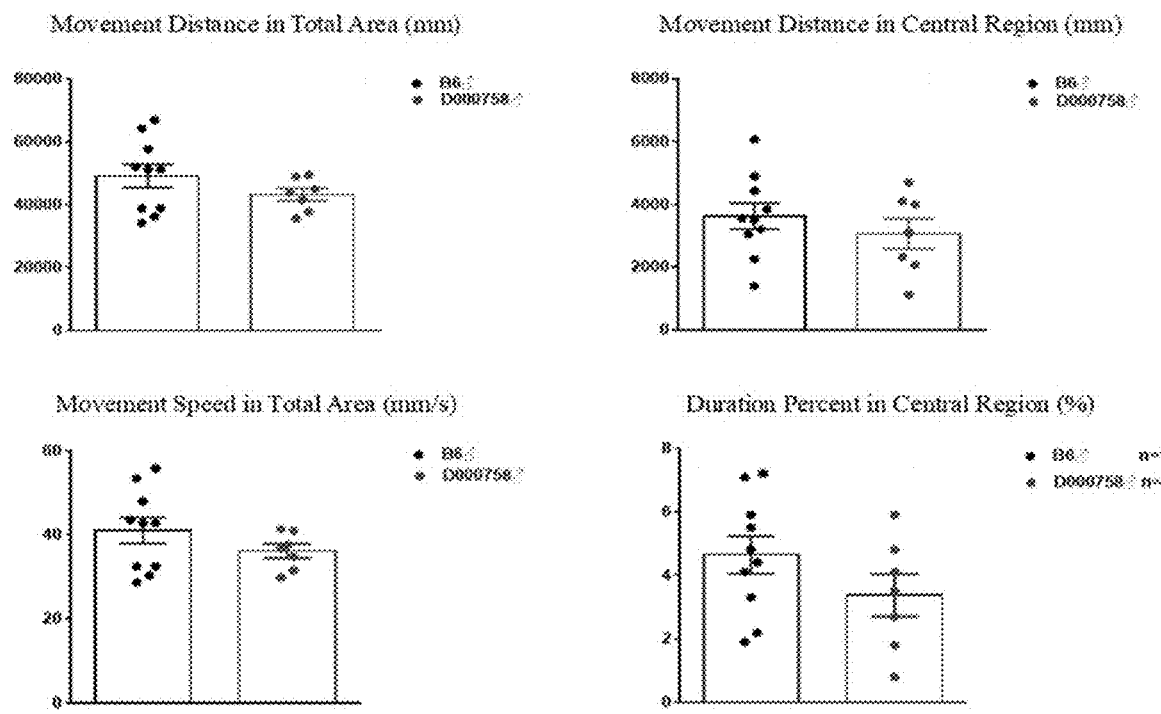
FIG. 1 to FIG. 4 show the results of the open field test of the mouse with high intelligence level of the present application.
Figure 2:
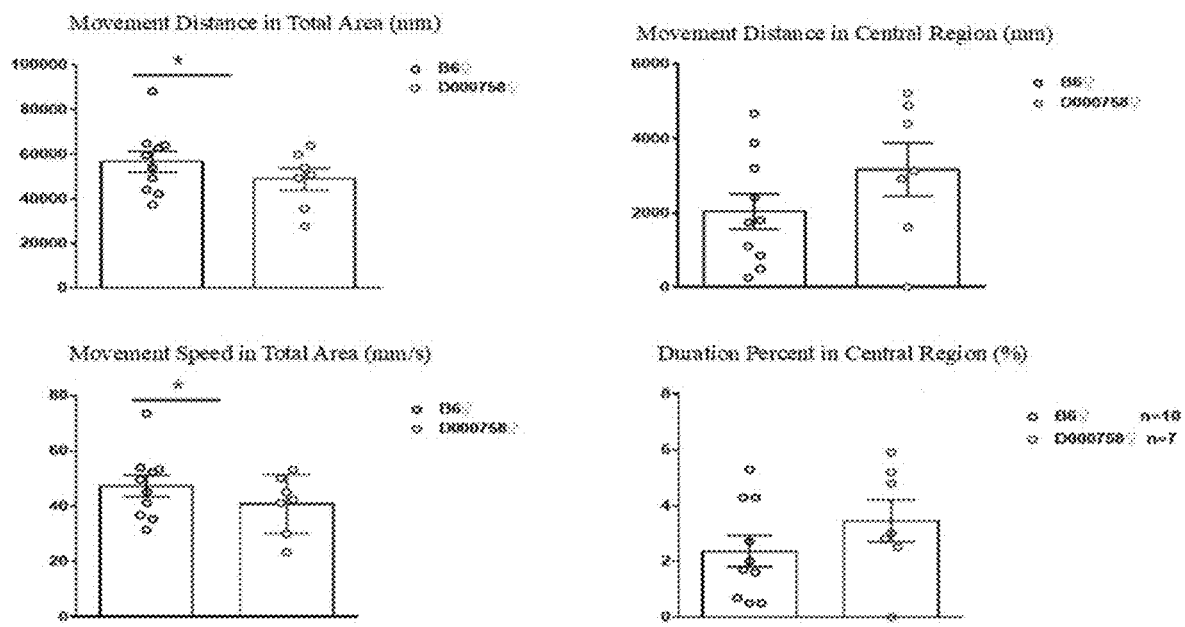
Figure 3:
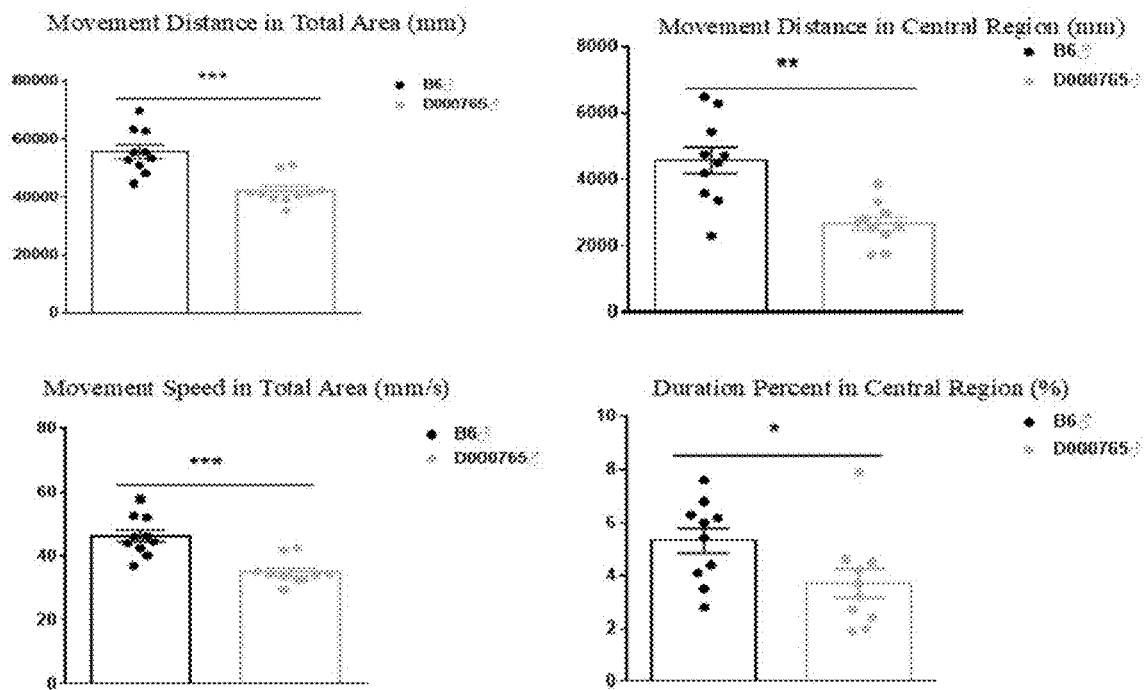
Figure 4:
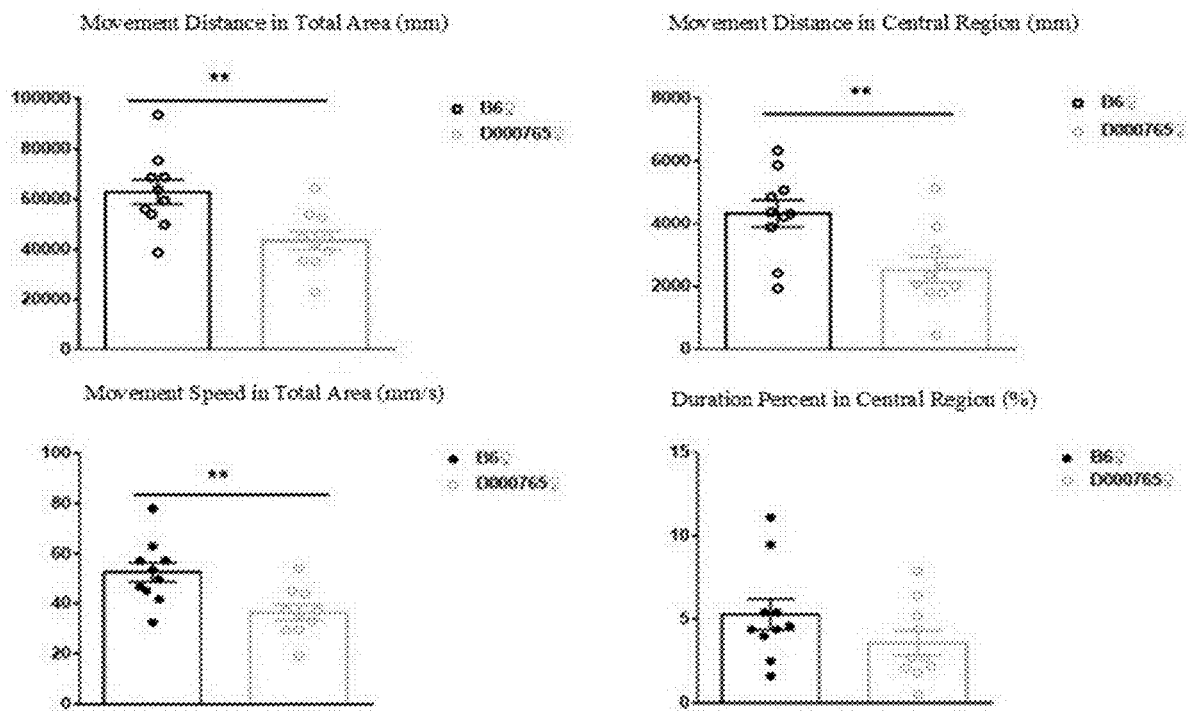

Hereinafter the embodiments of the invention of the present application are described by specific examples. Those skilled in the art can easily understand other advantages and effects of the invention of the present application from the disclosure in the specification.

The Term

In the present application, the term "mouse model" generally refers to usable animal models which can include not only mouse (Mus musculus), but also cells, tissues, or other materials derived therefrom.

In the present application, the term "wide-type mice/mouse" generally refers to wild-type mice (WT) whose phenotype of genetic characteristics in naturally-occurring population is considered as "normal (normal)" type. Similarly, the allele of a specific gene conferring this phenotype is considered as "normal (normal)" type in the naturally-occurring population. For example, the wild-type mouse can include mice captured from various places growing in a natural state.

In the present application, the term "high intelligence level" generally refers to a significantly increased intelligence level as compared with normal state. The intelligence level can be measured by the Wechsler Adult Intelligence Scale. For example, the intelligence level with the score being greater than 120 is considered as high intelligence level. The intelligence level of mouse can also be measured via experiments, e.g., by open field test, sucrose preference test, water maze evaluation test, space exploration Y maze test, and/or active avoidance Y maze test. Other methods of measuring the intelligence level of mouse are also known for persons skilled in the art. See, e.g., Matzel, L. M. et al. Individual differences in the expression of a 'general' learning ability in mice. Journal of Neuroscience, 23, 6423-6433, (2003).

In the present application, the term "all or a portion of chromosomes" generally refers to a complete chromosome or its fragment. The chromosome can be a configuration composed of double helix DNA and histone which is unique to eukaryotes. The chromosome can be a polymer formed by deep compression of genetic materials having genetic properties in the cells. In the interphase, the chromosome can be present in a form of chromatin. The mouse can have 20 pairs of chromosomes.

In the present application, the term "replacing/replace/replacement" generally refers to the replacement of a chromosome of mouse with a complete chromosome or its fragment originated from wild-type mouse. For example, the replacement can be that the mouse includes a complete chromosome or its fragment originated from wild-type mouse. On that basis, the replacement can also be that the corresponding original chromosome of the mouse is substituted, and/or loses a function that it exerts. A method for performing the replacement is known by persons skilled in the art, e.g., by means of hybridization and/or gene editing.

In the present application, the term "gene editing" generally refers to a technology for carrying out the insertion, deletion, modification, or replacement of DNA. The gene editing can utilize Zinc Finger Nucleases (ZFNs), Transcription Activator Like Effector Nuclease (TALEN) or CRISPR-Cas9 system. For example, the gene editing can include a knock-in approach. The knock-in approach can be an operational approach commonly used by persons skilled in the art, see, e.g., "Gene Targeting: A Practical Approach", edited by Joyner, Oxford University Press Ltd., 2000.

In the present application, the term "specific SNP site" generally refers to an SNP site specific to a certain genotype. The SNP site can be a position of nucleic acid which reflects the single nucleotide polymorphism (Single Nucleotide Polymorphism). In the present application, the SNP can refer to a change in DNA sequence caused by a change of a single nucleotide—A, T, C, or G. A typical SNP site can be two alleles. The SNP site can be located in a non-coding area, and/or a coding area. The method for detecting the SNP site can be selected from the group consisting of DNA sequencing, single-stranded conformation polymorphism (SSP), electrochemical analysis, denatured HPLC and gel electrophoresis, restriction fragment length polymorphism, and hybridization analysis.

In the present application, the term "primary cell culture" generally refers to a product obtained by culturing primary cells. The primary cells can be originated from an excised animal tissue. The isolated primary cells can include adherent cells which need to grow by attachment and suspension cells which can grow without attachment. The primary cell culture can be obtained by in vitro culture after the dissociation (e.g., by enzymatic treatment) of the primary cells. The culture of the primary cell can be transformed into infinite passage culture.

In the present application, the term "motor ability" generally refers to an ability to participate in sports and training. The motor ability can include aerobic ability, muscular strength, physical flexibility, balance ability, and reactive ability. The motor ability can be a comprehensive performance of many factors, e.g., physical morphology, quality, skills, techniques, techniques and mental ability, etc.

In the present application, the term "emotional state" generally refers to psycho-physiological constructs (psycho-physiological constructs), which includes cognition, conation, and emotion. The emotional state can vary in three primary aspects: valence (valence), arousal (arousal), and motivational salience (Motivational salience) (see Current Directions in Psychological Science. 2013-8, 22(4): 301-307). In the present application, the emotional state can include depression, prudence, and other features.

In the present application, the term "leaning ability" generally refers to psychological characteristics possessed by an individual to engage in leaning activities. The learning ability can include imagination, attention, perception observation ability, reading ability, analysis ability, operation ability, adaptability ability, induction and summarization ability, problem-solving ability, or any combination thereof.

In the present application, the term "memory ability" generally refers to the ability to memorize, maintain, re-recognize and reproduce the content and experience reflected by an objective thing. The memory ability can include sensory memory ability, short-term memory ability, and long-term memory ability.

In the present application, the term "space exploration ability" generally refers to an ability to explore the shape and/or position of an object. The space exploration ability includes observing, considering, imagining, cognizing and/or seeking the shape and/or position of an object.

In the present application, the term "Alzheimer's disease" generally refers to presenile dementia or aged dementia, which is a neurodegenerative disease with slow onset and worsening over time. The most common early symptom is loss of short-term memory (difficulty in remembering recent events). As the disease progresses, at least one of the following symptoms may gradually occurs: language disorder, disorientation (e.g., easy to get lost), emotional instability, loss of motivation, inability to care for oneself, and behavioral problems. The true cause of the Alzheimer's disease is still unknown, and its progression is related to the deposition of fibrous amyloid plaques and Tau protein in the brain. At present, there is no therapy that can prevent or reverse the course of disease, but only a few methods may temporarily relieve or improve symptoms.

In the present application, the term "chronic encephalopathy syndrome" generally refers to an organic syndrome transformed from a slowly progressing brain lesion or acute encephalopathy syndrome. The main clinical manifestations are dementia, personality change and amnesia syndrome without disturbance of consciousness. It may be accompanied by chronic psychiatric symptoms, such as depression, mania-like or schizophrenia-like performance. The chronic encephalopathy syndrome can be caused by chronic organic diseases, or can be seen in the sequelae caused by delayed acute encephalopathy syndrome.

In the present application, the term "attention deficit disorder" is also known as Attention Deficit Disorder (ADD) or attention deficit hyperactivity disorder (ADHD), which can include adult attention deficit disorders and/or childhood attention deficit disorders. The attention deficit disorders can be characterized by difficulty to focus, hyperactivity, doing things without considering the consequences, etc. In addition, there are problems including age-inappropriate behavior and difficulty for emotional regulations in attention-deficit individuals. The attention deficit disorder can be caused by the interaction of gene, environment, society and other factors.

In the present application, the term "childhood autism" is also known as childhood-autism, which begins before the age of 3 and is a psychological development disorder primarily characterized by social interaction disorder, communication disorder and limited, stereotyped and repetitive behaviors, and is the most representative disease among the generalized development disorders. In the present application, the childhood autism can include childhood autism, Asperge's syndrome, Rett's syndrome, childhood disintegrative disorder, atypical autism and/or other unspecified generalized developmental disorder. Childhood autism is a psychological developmental disorder caused by many factors and having a biological basis. It is a disease of individuals with genetic susceptibility occurring under the action of specific environmental factors. Children patients exhibit disorders in social interaction, communication etc., have restricted interests, and tend to repeat rigid behaviors.

In the present application, the term "mental retardation (MR)" generally refers to the persistent impairment of cognitive activity and/or the impairment of the whole psychological activity. The mental retardation can be caused by organic damage to the brain caused by influencing factors (e.g., genetic variation, infection, poisoning, head injury, brain malformation or endocrine abnormality) or by incomplete brain development.

DETAILED DESCRIPTION OF THE INVENTION

Mouse Model with High Intelligence Level, Construction Method and Use Thereof

In an aspect, the present application provides a method of constructing a mouse model with high intelligence level, including replacing chromosomes in a mouse with all or a portion of chromosomes originated from wild-type mouse, such that the mouse becomes a mouse with high intelligence level.

In the present application, the wild-type mouse may be originated from strains selected from the group consisting of BLD, CM, DX, FX, HZ, JD, KM, PD, QP, SMX, SY, TW, TZ, YP, YX, ZC, ZZ1 and ZZ2.

In the present application, the specific numbers and strain names of the wild-type mouse sources are shown in Table 1.

TABLE 1

Specific Numbers and Strain Names of Wild-Type Mouse Sources

| CS Strains | Areas | Strain Numbers | Strain Names |
|---|---|---|---|
| CSS1 | Jiading-JD | D000748 | B6/J-Chr1JD (jhxiao)/Nju |
| CSS2 | Songjiang-SJ | D000749 | B6/J-Chr1SJ (jhxiao)/Nju |
| CSS3 | Yangpu-YP | D000750 | B6/J-Chr1YP (jhxiao)/Nju |
| CSS9 | Linyi-LY | D000756 | B6/J-Chr1LY (jhxiao)/Nju |
| CSS10 | Chongming-CM | D000757 | B6/J-Chr1CM (jhxiao)/Nju |
| CSS11 | Balidian-BLD | D000758 | B6/J-Chr1BLD (jhxiao)/Nju |
| CSS12 | Tianwang-TW | D000759 | B6/J-Chr1TW (jhxiao)/Nju |
| CSS20 | Hangzhou-HZ | D000767 | B6/J-Chr1HZ (jhxiao)/Nju |
| CSS24 | Kunming-KM | D000771 | B6/J-Chr1KM (jhxiao)/Nju |
| CSS25 | Daxin-DX | D000772 | B6/J-Chr1DX (jhxiao)/Nju |
| CSS18 | Zaozhuang 2-ZZ2 | D000765 | B6/J-Chr12-ZZ2 (jhxiao)/Nju |

For example, C57BL/6J represents a subline of C57BL maintained by the Jackson laboratories in the United States, which may be abbreviated as B6/J.

In the present application, the mouse may be originated from Strain C57BL/6J.

In the present application, the replacement may include crossing with the wild-type mouse.

In the present application, the replacement may include the following steps:
  a) crossing the mouse with the wild-type mouse to obtain F1, backcrossing the F1 with the mouse to obtain F2, and screening out mice with at least one chromosome in heterozygous state from the F2;
  b) continuously backcrossing the mice with chromosome in heterozygous state screened in step a) with the mouse, and screening out mouse population with mouse genotype in which the chromosome is heterozygous and other chromosomes are homozygous; and
  c) using the mouse population screened out in step b) as an inbred line, and obtaining the mouse model by selfing.

The replacement method can be known by persons skilled in the art. For example, it is feasible to obtain a mouse in which chromosome 1 is replaced based a wild-type mouse (e.g., ZZ2 mouse) source by reference to the method as described in CN 104170792B.

For example, the replacement may include the following steps:
  (1) ZZ2 mice were crossed with mice C57BL/6J to obtain an F1 passage. The F1 passage mice were back-crossed with C57BL/6J to obtain an F2 passage. The F2 passage mice were subject to genotyping to screen out those in which the DNA sequence of the whole chromosome 1 is heterozygous.
  (2) The F2 passage mice were back-crossed with C57BL/6J. After backcrossing in the same manner and screening for 10 passages, a mouse population having a C57BL/6J genotype in which the DNA sequence of chromosome 1 was heterozygous while the remainder chromosomes were homozygous was formed.

(3) The back-crossed mice were identified for their gene DNA.

(4) The back-crossed mice with the chromosome 1 in the heterozygous state of ZZ2 and B6 were bred to a homologous gene introduced inbred line carrying the chromosome 1 of ZZ2 mice. By sibling selfing and screening by gene identification, the mice with high intelligence level of the present application (e.g., D000765 mice) can be obtained.

Alternatively, for example, the replacement may include the following steps:

(1) BLD mice were crossed with mice C57BL/6J to obtain an F1 passage. The F1 passage mice were back-crossed with C57BL/6J to obtain an F2 passage. The F2 passage mice were subject to genotyping to screen out those in which the DNA sequence of the whole chromosome 1 is heterozygous.

(2) The F2 passage mice were back-crossed with C57BL/6J. After backcrossing and screening in the same manner for 10 passages, a mouse population having a C57BL/6J genotype in which the DNA sequence of chromosome 1 was heterozygous while the remainder chromosomes were homozygous was formed.

(3) The back-crossed mice were identified for their gene DNA.

(4) The back-crossed mice with the chromosome 1 in the heterozygous state of BLD and B6 were bred to a homologous gene introduced inbred line carrying the chromosome 1 of BLD mice. By sibling selfing and screening by gene identification, the mice with high intelligence level of the present application (e.g., D000758 mice) can be obtained.

In the present application, the screening may include genotyping. The genotyping may be a process of detecting the DNA sequence of an individual by use of a biological test. For example, the gene analysis may be comparing the target sequence with a sequence from another individual or a reference sequence to determine a difference in genetic organization (genotype) of the individual. The genotyping method may be a conventional method in the art, e.g., identification of Single Nucleotide Polymorphism (Single Nucleotide Polymorphism), Restriction Fragment Length Polymorphism (Restriction Fragment Length Polymorphism, RFLP), Terminal Restriction Fragment Length Polymorphism (Terminal Restriction Fragment Length Polymorphism, t-RFLP), Amplified fragment length polymorphisms (Amplified fragment length polymorphisms, AFLP) and/or multiplex ligation-dependent probe amplification (multiplex ligation-dependent probe amplification, MLPA). The technical means of gene analysis may be conventional technical means in the art, such as, polymerase chain reaction (PCR), DNA fragment analysis, oligonucleotide probes (ASO probes), gene sequencing, nucleic acid hybridization and/or gene chip technology.

In the present application, the screening may include identifying specific SNP sites of the chromosome of the wild-type mouse. For example, it is feasible to detect the SNP sites as stated in Table 2 of CN 104170792B to identify whether the chromosome 1 or its fragment originated from the wild-type mouse (e.g., ZZ2 mouse) has been replaced into the mouse genome; and/or identify that the genome of the mouse with high intelligence level includes chromosome 1 or its fragment originated from the wild type mouse (e.g., ZZ2 mouse).

In the present application, the chromosomes may include chromosome 1. The chromosome 1 of wild-type mice can be referred to the disclosure of Michael F. Seldin et al., Mammalian Genome volume 1, pages S1-S17 (1991).

In the present application, the replacement may include means of gene editing. For example, the original chromosome 1 or its fragment of mouse may be knock-out by means of gene editing (e.g., CRISPR-Cas); or the mouse may include chromosome 1 or its fragment originated from the wild-type mouse (e.g., ZZ2 mouse) by means of knock-in. For example, the mouse may include chromosome 1 or its fragment originated from the wild-type mouse (e.g., ZZ2 mouse) with the aid of a plasmid (which may include the nucleotide sequence encoding chromosome 1 or its fragment originated from the wild-type mouse (e.g., ZZ2 mouse)). Alternatively, for example, the original chromosome 1 or its fragment of the mouse may reduce or lose its original function by virtue of RNAi or similar means.

In the present application, the high intelligence level may be determined by evaluating one or more conditions selected from the group consisting of motor ability, emotional state, learning ability, memory ability and space exploration ability.

In the present application, the emotional state may include an evaluation factor selected from the group consisting of anxiety or not, depression or not, and prudence or not. The mouse with high intelligence level of the present application may be prudent, non-anxious, and/or non-depressed.

In the present application, the emotional state may be evaluated by the sucrose preference test. If the emotional state of mouse is problematic and/or disturbed, its preference for sucrose will be reduced; in the contrast, the mouse with high intelligence level should maintain a preference for sucrose at normal level. It is feasible to evaluate the preference degree of mouse for sucrose by calculating the preference index for sucrose, and then evaluate the emotional state of mice: the preference index of sucrose %=sucrose consumption/(sucrose consumption+pure water consumption)×100%.

In the present application, the learning ability and/or the memory ability may be evaluated by the water maze test. The water maze test (e.g., Morris water maze) can force the mouse to swim to learn to find a platform hidden in water, so as to test the learning ability and/or memory ability of the mouse for senses of spatial position and direction. Water maze test may also include acquisition training, exploration training, counterpoint training or counterpoint exploration training. The shorter the time period from entering the water to finding the platform, the shorter the displacement distance in the period, and correspondingly the higher the intelligence level of mice. Water maze evaluation test can be an important experiment to evaluate the intelligence level of mice.

In the present application, the space exploration ability and/or the memory ability may be evaluated by the space exploration Y maze test. The space exploration Y maze may consist of three identical arms with a food providing device at the end of each arm. When mice search for food in the maze, they can remember the maze arm which they have searched according to the visual signs around the maze, so as to avoid repeatedly entering the same arm, and obtain food effectively. The space exploration Y maze test may evaluate the recognition and memory abilities of mice to new environment. At the same time, if the mice behaviors are relatively prudent in the space exploration Y maze test, it also means that the mouse has a relatively high intelligence level.

In the present application, the memory ability may be evaluated by the active avoidance Y maze test. The active avoidance Y maze test may consist of three arms, wherein some arms are relatively safe (i.e., a safe area), while the other arms can be powered up so as to produce a sufficient current for the mouse to escape. During the experiment, the safe area is changed; the mouse is shocked; immediate escape of mouse from the safe area is recorded as one correct reaction; and several continuous correct reactions of the mouse during the train process are "learned". The less the training times required by "learning", the higher the intelligence level of the mouse. The active avoidance Y maze test may reflect the memory ability of mice for fear.

In the present application, the motor ability may be evaluated by the open field test and/or the fatigue rotarod test.

In the present application, the open field test is an approach for evaluating the autonomous behavior, inquiry behavior and tension of experimental animals in an unfamiliar environment. If a mouse does not actively go to the central region (i.e., the mouse does not tend to explore casually and/or be excessively tense or relax in an unfamiliar environment), the mouse tends to be prudent, or the mouse may be considered to have a high intelligence level. At the same time, the open field test may evaluate the motor ability of the mouse, namely, it may evaluate that the mouse possesses normal mobility and reaction speed.

In the present application, the fatigue rotarod test may evaluate the motor ability of the mouse, especially may evaluate the motor coordination and fatigue resistance of the mouse. The results of the fatigue rotarod test may reflect that the mouse with high intelligence level is not significantly different from the control mouse (e.g., the C57BL/6J mouse) in the motor ability.

In another aspect, the present application provides a mouse model with high intelligence level constructed by the method of the present application.

In another aspect, the present application provides a mouse model with high intelligence level, wherein the chromosomes of the mouse at least include all or a portion of the chromosomes originated from the wild-type mouse.

In the present application, the wild-type mouse may be originated from strains selected from the group consisting of BLD, CM, DX, FX, HZ, JD, KM, PD, QP, SMX, SY, TW, TZ, YP, YX, ZC, ZZ1 and ZZ2.

In the present application, the mouse may be originated from a strain selected from the group consisting of C57BL/6J.

In the present application, the mouse may include all or a portion of chromosome 1 originated from the wild-type mouse.

In the present application, the high intelligence level may be determined by evaluating one or more conditions selected from the group consisting of motor ability, emotional state, learning ability, memory ability and space exploration ability.

In the present application, the emotional state may be evaluated by the sucrose preference test.

In the present application, the learning ability and/or the memory ability may be evaluated by the water maze test.

In the present application, the space exploration ability and/or the memory ability may be evaluated by the space exploration Y maze test.

In the present application, the memory ability may be evaluated by the active avoidance Y maze test.

In the present application, the motor ability may be evaluated by the open field test and/or the fatigue rotarod test.

In the present application, the mouse in the mouse model with high intelligence level (i.e., the mouse with high intelligence level) may possess higher intelligence level as compared with the control mouse (e.g., C57BL/6J mouse). For example, the mouse with high intelligence level may be more prudent, non-cautious, non-depressed, and possess better emotional ability; have better learning ability, especially learning ability against senses of spatial position and direction; have better memory ability including both the memory ability against senses of spatial direction and direction and the memory ability regarding fear; and/or possess better space exploration ability. Alternatively, for example, the motor ability of the mouse with high intelligence level may be not significantly different from that of the control mouse (e.g., the C57BL/6J mouse). Therefore, the mouse of the mouse model with high intelligence level may have a higher intelligence level in a stable and good emotional state.

In another aspect, the present application provides use of the mouse model with high intelligence level of the present application for preparing a mouse model with deficient intelligence level.

In the present application, the system may be used to identify material that is able to influence the intelligence level.

In another aspect, the present application provides a system of identifying material that is able to influence the intelligence level, the system including a mouse model with high intelligence level in which the mouse chromosomes of the mouse model with high intelligence level at least include all or a portion of the chromosome originated from the wild-type mouse.

In the present application, the wild-type mouse may be originated from strains selected from the group consisting of BLD, CM, DX, FX, HZ, JD, KM, PD, QP, SMX, SY, TW, TZ, YP, YX, ZC, ZZ1 and ZZ2.

In the present application, the mouse may be originated from a strain selected from the group consisting of C57BL/6J.

In the present application, the mouse in the mouse model with high intelligence level may include all or a portion of chromosome 1 originated from the wild-type mouse.

In the present application, the system may include an identification module for identifying the influence of the material on the intelligence level of the mouse model with high intelligence level.

In the present application, the identification module may include a reagent and/or instrument for identifying the influence of the material on the intelligence level of the mouse model with high intelligence level.

In the present application, the identification module may include a reagent and/or instrument required by a test selected from the group consisting of open field test, sucrose preference test, water maze test, space exploration Y maze test, active avoidance Y maze test and the fatigue rotarod test. For example, the identification module may include a reagent and/or instrument selected from the group consisting of observation box, sucrose solution, water (including dyed water), water maze (e.g., including a hidden underwater platform), Y maze (e.g., trisection radial maze box), a trisection arm reflection box (e.g., including a clicking device), and a Fatigue RotaRod System.

In the present application, the identification module may determine the influence of the material on the activity and/or expression of intelligence level associated protein.

For example, the identification module may include a reagent and/or instrument that can determine an activity and/or expression of the intelligence level associated protein. In the present application, the identification module may include a reagent and/or instrument for determining the influence of the material on the activity and/or expression of the intelligence level associated protein.

In the present application, the identification module may include a reagent that can specifically recognize the intelligence level associated protein (e.g., the reagent may include an antibody and/or ligand that specifically bind(s) to the intelligence level associated protein), and/or material that can determine the activity of the intelligence level associated protein (e.g., the material may be an enzyme that has an activity associated with the activity of the intelligence level associated protein, and/or proteins and/or transcription factors that have an activity associated with the upstream and downstream reactor pathways of the intelligence level associated protein).

In the present application, the identification module may include a reagent and/or instrument for determining the influence of the material on the activity and/or expression level of the nucleic acid encoding the intelligence level associated protein.

For example, the identification module may include a reagent and/or instrument that can determine the activity and/or expression of the nucleic acid encoding the intelligence level associated protein. In the present application, the identification module may include a primer that can specifically expand the nucleic acid encoding the intelligence level associated protein, and/or a probe that can specifically recognize the nucleic acid encoding the intelligence level associated protein (e.g., the probe may be a dsDNA probe, an ssDNA probe, an aptamer, or an RNAi).

In another aspect, the present application provides a method of evaluating the influence of material on the intelligence level, and the method may include administering a candidate material to a mouse model with high intelligence level, wherein the chromosomes of the mouse model with high intelligence level at least include all or a portion of the chromosome originated from the wild-type mouse.

In the present application, the mouse in the mouse model with high intelligence level may include all or a portion of chromosome 1 originated from the wild-type mouse.

In the present application, the wild-type mouse may be originated from strains selected from the group consisting of BLD, CM, DX, FX, HZ, JD, KM, PD, QP, SMX, SY, TW, TZ, YP, YX, ZC, ZZ1 and ZZ2.

In the present application, the mouse may be originated from a strain selected from the group consisting of C57BL/6J.

In the present application, the administration may include injection, oral and/or topical administration.

In the present application, the material may be candidate drugs for preventing and/or treating the intelligence level associated diseases. For example, the intelligence level associated diseases may include Alzheimer's disease, chronic encephalopathy syndrome, attention deficit disorder, childhood autism and mental retardation (MR).

In the present application, the method may include the step of evaluating the influence of the material on the intelligence level of the mouse model with high intelligence level.

In the present application, the intelligence level may be determined by evaluating one or more conditions selected from the group consisting of motor ability, emotional state, learning ability, memory ability and space exploration ability. For example, the intelligence level may be determined by performing a test selected from the group consisting of open field test, sucrose preference test, water maze test, space exploration Y maze test, active avoidance Y maze test and the fatigue rotarod test.

In the present application, the evaluation may include evaluating the influence of the material on the intelligence level of the mouse model with high intelligence level. For example, if the intelligence level of the mouse in the mouse model with high intelligence level is remarkably decreased after the material is administered, it may be considered that the material can be reduced and/or damage the intelligence level of the mouse in the mouse model with high intelligence level. Alternatively, for example, if the intelligence level of the mouse in the mouse model with high intelligence level is not significantly changed and/or decreased after the material is administered, it may be considered that the material would not decrease and/or damage the intelligence level the mouse in the mouse model with high intelligence level. The material may also be considered to be safe for the mouse in the field of intelligence level. Alternatively, for example, if the intelligence level of the mouse in the mouse model with high intelligence level is significantly increased after the material is administered, it may be considered that the material may increase the intelligence level of the mouse in the mouse model with high intelligence level.

The system of the present application and/or the method of the present application may be used to screen and/or evaluate if a material will produce a negative effect on the intelligence level; and may also be used for the detection of safety.

In the present application, the evaluation may include evaluating the influence of the material on the activity and/or expression of intelligence level associated protein.

For example, it is feasible to use a reagent that can specifically recognize the intelligence level associated protein (e.g., the reagent may include an antibody and/or ligand that specifically bind(s) to the intelligence level associated protein), and/or a material that can determine the activity of the intelligence level associated protein (e.g., the material may be an enzyme that has an activity associated with the activity of the intelligence level associated protein, and/or proteins and/or transcription factors that have an activity associated with the upstream and downstream reactor pathways of the intelligence level associated protein) to evaluate the influence of the material on the activity and/or expression of the intelligence level associated protein.

In the present application, the evaluation may include evaluating the influence of the material on the activity and/or expression of the nucleic acid encoding the intelligence level associated protein.

For example, it is feasible to use a reagent and/or instrument that can determine the activity and/or expression of the nucleic acid encoding the intelligence level associated protein to evaluate the activity and/or expression of the nucleic acid encoding the intelligence level associated protein. For example, the agent may include a primer that can specifically expand the nucleic acid encoding the intelligence level associated proteins, and/or a probe that can specifically recognize the nucleic acid encoding the intelligence level associated proteins (e.g., the probe can be a dsDNA probe, an ssDNA probe, an aptamer, or an RNAi).

The present application further relates to the following embodiments:

1. A method of constructing a mouse model with high intelligence level, including replacing a chromosome in a mouse with all or a portion of a chromosome originated from wild-type mouse, so that the mouse becomes a mouse with high intelligence level.
2. The method according to embodiment 1, wherein the wild-type mouse is originated from strains selected from the group consisting of BLD, CM, DX, FX, HZ, JD, KM, PD, QP, SMX, SY, TW, TZ, YP, YX, ZC, ZZ1 and ZZ2.
3. The method according to any one of embodiments 1-2, wherein the mouse is originated from a strain selected from the group consisting of C57BL/6J.
4. The method according to any one of embodiments 1-3, wherein the replacement includes crossing with the wild-type mouse.
5. The method according to any one of embodiments 1-4, wherein the replacement includes using gene editing means.
6. The method according to any one of embodiments 1-5, wherein the replacement includes the following steps:
   a) crossing the mouse with the wild-type mouse to obtain F1, backcrossing the F1 with the mouse to obtain F2, and screening out mice with at least one chromosome in heterozygous state from the F2;
   b) continuously backcrossing the mice with chromosome in heterozygous state screened in step a) with the mouse, and screening out mouse population with mouse genotype in which the chromosome is heterozygous and other chromosomes are homozygous; and
   c) using the mouse population screened out in step b) as an inbred line, and obtaining the mouse model by selfing.
7. The method according to embodiment 6, wherein the screening includes genotyping.
8. The method according to any one of embodiments 6-7, wherein the screening includes identifying a specific SNP site of a chromosome of a wild-type mouse.
9. The method according to any one of embodiments 1-8, wherein the chromosome includes chromosome 1.
10. The method according to any one of embodiments 1-9, wherein the high intelligence level is determined by evaluating one or more conditions selected from the group consisting of motor ability, emotional state, learning ability, memory ability and space exploration ability.
11. The method according to embodiment 10, wherein the emotional state is evaluated by the sucrose preference test.
12. The method according to any one of embodiments 10-11, wherein the learning ability and/or the memory ability are/is evaluated by the water maze test.
13. The method according to any one of embodiments 10-12, wherein the space exploration ability and/or the memory ability are/is evaluated by the space exploration Y maze test.
14. The method according to any one of embodiments 10-13, wherein the memory ability is evaluated by the active avoidance Y maze test.
15. The method according to any one of embodiments 10-14, wherein the motor ability is evaluated by the open field test and/or the fatigue rotarod test.
16. A mouse model with high intelligence level constructed by the method of any one of embodiment 1-15.
17. A mouse model with high intelligence level, wherein the chromosome of the mouse at least includes all or a portion of chromosome originated from the wild-type mouse.
18. The mouse model with high intelligence level according to embodiment 17, wherein the wild-type mouse is originated from strains selected from the group consisting of BLD, CM, DX, FX, HZ, JD, KM, PD, QP, SMX, SY, TW, TZ, YP, YX, ZC, ZZ1 and ZZ2.
19. The mouse model with high intelligence level according to any one of embodiments 17-18, wherein the mouse is originated from a strain selected from the group consisting of C57BL/6J.
20. The mouse model with high intelligence level according to any one of claims 17-19, wherein the mouse includes all or a portion of chromosome 1 originated from the wild-type mouse.
21. The mouse model with high intelligence level according to any one of embodiments 17-20, wherein the high intelligence level is determined by evaluating one or more conditions selected from the group consisting of motor ability, emotional state, learning ability, memory ability and space exploration ability.
22. The method according to embodiment 21, wherein the emotional state is evaluated by the sucrose preference test.
23. The mouse model with high intelligence level according to any one of embodiments 21-22, wherein the learning ability and/or the memory ability are/is evaluated by the water maze test.
24. The mouse model with high intelligence level according to any one of embodiments 21-23, wherein the learning ability and/or the memory ability are/is evaluated by the water maze test.
25. The mouse model with high intelligence level according to any one of embodiments 21-24, wherein the space exploration ability and/or the memory ability are/is evaluated by the space exploration Y maze test.
26. The mouse model with high intelligence level according to any one of embodiments 21-25, wherein the memory ability is evaluated by the active avoidance Y maze test.
27. The mouse model method with high intelligence level according to any one of embodiments 21-26, wherein the motor ability is evaluated by the open field test and/or the fatigue rotarod test.
28. Use of the mouse model with high intelligence level according to any one of claims 17-27 for preparing a mouse model with deficient intelligence level.
29. Use of the mouse model with high intelligence level according to any one of claims 17-27 for preparing a system for identifying a material that is able to influence the intelligence level.
30. A system of identifying material that is able to influence the intelligence level, wherein the system includes a mouse model with high intelligence level in which the chromosomes of the mouse model with high intelligence level at least include all or a portion of the chromosome originated from the wild-type mouse.
31. The system according to embodiment 30, wherein the wild-type mouse is originated from strains selected from the group consisting of BLD, CM, DX, FX, HZ, JD, KM, PD, QP, SMX, SY, TW, TZ, YP, YX, ZC, ZZ1 and ZZ2.
32. The system according to any one of embodiments 30-31, wherein the mouse is originated from a strain selected from the group consisting of C57BL/6J.
33. The system according to any one of embodiments 30-32, wherein the mouse in the mouse model with high intelligence level includes all or a portion of chromosome 1 originated from the wild-type mouse.
34. The system according to any one of embodiments 30-33, wherein the system includes an identification module for identifying the influence of the material on the intelligence level of the mouse model with high intelligence level.

35. The system according to embodiment 34, wherein the identification module includes a reagent and/or instrument for identifying the influence of the material on the intelligence level of the mouse model with high intelligence level.

36. The system according to any one of embodiments 34-35, wherein the identification module includes a reagent and/or instrument required by a test selected from the group consisting of open field test, sucrose preference test, water maze test, space exploration Y maze test, active avoidance Y maze test and the fatigue rotarod test.

37. The system according to any one of embodiments 34-36, wherein the identification module determines the influence of the material on the activity and/or expression of intelligence level associated protein.

38. The system according to any one of embodiments 34-37, wherein the identification module includes a reagent and/or instrument for determining the influence of the material on the activity and/or expression level of the intelligence level associated protein.

39. The system according to any one of embodiments 34-38, wherein the identification module includes a reagent that can specifically recognize the intelligence level associated protein, and/or a material that can determine the activity of the intelligence level associated protein.

40. The system according to any one of embodiments 34-39, wherein the identification module includes a reagent and/or instrument for determine the influence of the material on the activity and/or expression level of a nucleic acid encoding the intelligence level associated protein.

41. The system according to any one of embodiments 34-40, wherein the identification module includes a primer that can specifically expand the nucleic acid encoding the intelligence level associated protein, and/or a probe that can specifically recognize the nucleic acid encoding the intelligence level associated protein.

42. A method of evaluating an influence of a material on the intelligence level, including administering a candidate material in which the mouse chromosome of the mouse model with high intelligence level at least includes all or a portion of the chromosome originated from the wild-type mouse.

43. The method according to embodiment 42, wherein the wild-type mouse is originated from strains selected from the group consisting of BLD, CM, DX, FX, HZ, JD, KM, PD, QP, SMX, SY, TW, TZ, YP, YX, ZC, ZZ1 and ZZ2.

44. The method according to any one of embodiments 42-43, wherein the mouse is originated from a strain selected from the group consisting of C57BL/6J.

45. The method according to any one of embodiments 42-44, wherein the mouse in the mouse model with high intelligence level includes all or a portion of chromosome 1 originated from the wild-type mouse.

46. The method according to any one of embodiments 42-45, wherein the administration includes injection, oral, and/or topical administration.

47. The method according to any one of embodiments 42-46, including the step of evaluating the influence of the material on the intelligence level of the mouse model with high intelligence level.

48. The method according to embodiment 47, wherein the evaluation includes identifying the influence of the material on the intelligence level of the mouse model with high intelligence level.

49. The method according to any one of embodiments 47-48, wherein the evaluation includes performing a test selected from the group consisting of open field test, sucrose preference test, water maze test, space exploration Y maze test, active avoidance Y maze test and the fatigue rotarod test.

50. The method according to any one of embodiments 47-49, wherein the evaluation includes evaluating the influence of the material on the activity and/or expression of intelligence level associated protein.

51. The method according to any one of embodiments 47-50, wherein the evaluation includes evaluating the influence of the material on the activity and/or expression of a nucleic acid encoding the intelligence level associated protein.

Without being limited by any theory, the following examples are only for illustrating the fusion protein, preparation method, use of the present application or the like, and are not intended to limit the scope of the invention of the present application.

EXAMPLES

Example 1

Mice with high intelligence level (with the genotype of B6/J-Chr1BLD (jhxiao)/Gpt; or B6/J-Chr12-ZZ2 (jhxiao)/Gpt) and wild type mice (with the genotype of B6/J) as shown in Tables 2A and 2B are obtained, wherein the wild-type mice are used as control.

TABLE 2A

General Conditions of Mice with High Intelligence Level and Wild-Type Mice

| Strain Numbers | Gender | Ear Number | Birth Date | Age in Weeks | Genotypes | Hair Color |
|---|---|---|---|---|---|---|
| N000013 | ♂ | 646 | 2019 Jun. 8 | 6 | B6/J | Black |
|  |  | 647 | 2019 Jun. 8 | 6 | B6/J | Black |
|  |  | 648 | 2019 Jun. 8 | 6 | B6/J | Black |
|  |  | 649 | 2019 Jun. 8 | 6 | B6/J | Black |
|  |  | 643 | c2019 Jun. 8 | 6 | B6/J | Black |
|  |  | 695 | 2019 Jun. 8 | 6 | B6/J | Black |
|  |  | 696 | 2019 Jun. 8 | 6 | B6/J | Black |
|  |  | 697 | 2019 Jun. 8 | 6 | B6/J | Black |
|  |  | 698 | 2019 Jun. 8 | 6 | B6/J | Black |
|  |  | 699 | 2019 Jun. 8 | 6 | B6/J | Black |

TABLE 2A-continued

General Conditions of Mice with High Intelligence Level and Wild-Type Mice

| Strain Numbers | Gender | Ear Number | Birth Date | Age in Weeks | Genotypes | Hair Color |
|---|---|---|---|---|---|---|
| D000758 | ♂ | 170 | 2019 Jun. 5 | 6 | B6/J-Chr1BLD (jhxiao)/Gpt | Black |
| | | 171 | 2019 Jun. 5 | 6 | B6/J-Chr1BLD (jhxiao)/Gpt | Black |
| | | 172 | 2019 Jun. 5 | 6 | B6/J-Chr1BLD (jhxiao)/Gpt | Black |
| | | 173 | 2019 Jun. 5 | 6 | B6/J-Chr1BLD (jhxiao)/Gpt | Black |
| | | 137 | 2019 Jun. 5 | 6 | B6/J-Chr1BLD (jhxiao)/Gpt | Black |
| | | 138 | 2019 Jun. 5 | 6 | B6/J-Chr1BLD (jhxiao)/Gpt | Black |
| | | 139 | 2019 Jun. 5 | 6 | B6/J-Chr1BLD (jhxiao)/Gpt | Black |

TABLE 2B

General Conditions of Mice with High Intelligence Mice and Wild-Type Mice

| Strain Numbers | Gender | Ear Number | Birth Date | Age in Weeks | Genotypes | Hair Color |
|---|---|---|---|---|---|---|
| N000013 | ♀ | 620 | c2019 Jun. 8 | 6 | B6/J | Black |
| | | 622 | c2019 Jun. 8 | 6 | B6/J | Black |
| | | 623 | c2019 Jun. 8 | 6 | B6/J | Black |
| | | 624 | c2019 Jun. 8 | 6 | B6/J | Black |
| | | 644 | c2019 Jun. 8 | 6 | B6/J | Black |
| | | 665 | c2019 Jun. 8 | 6 | B6/J | Black |
| | | 666 | c2019 Jun. 8 | 6 | B6/J | Black |
| | | 667 | c2019 Jun. 8 | 6 | B6/J | Black |
| | | 668 | c2019 Jun. 8 | 6 | B6/J | Black |
| | | 669 | c2019 Jun. 8 | 6 | B6/J | Black |
| D000758 | ♀ | 164 | 2019 Jun. 5 | 6 | B6/J-Chr1BLD (jhxiao)/Gpt | Black |
| | | 165 | 2019 Jun. 5 | 6 | B6/J-Chr1BLD (jhxiao)/Gpt | Black |
| | | 166 | 2019 Jun. 5 | 6 | B6/J-Chr1BLD (jhxiao)/Gpt | Black |
| | | 167 | 2019 Jun. 5 | 6 | B6/J-Chr1BLD (jhxiao)/Gpt | Black |
| | | 156 | 2019 Jun. 5 | 6 | B6/J-Chr1BLD (jhxiao)/Gpt | Black |
| | | 162 | 2019 Jun. 5 | 6 | B6/J-Chr1BLD (jhxiao)/Gpt | Black |
| | | 163 | 2019 Jun. 5 | 6 | B6/J-Chr1BLD (jhxiao)/Gpt | Black |
| D000765 | ♂ | 900 | 2019 Jun. 15 | 5 | B6/J-Chr12-ZZ2 (jhxiao)/Gpt | Black |
| | | 910 | 2019 Jun. 15 | 5 | B6/J-Chr12-ZZ2 (jhxiao)/Gpt | Black |
| | | 901 | 2019 Jun. 15 | 5 | B6/J-Chr12-ZZ2 (jhxiao)/Gpt | Black |
| | | 902 | 2019 Jun. 15 | 5 | B6/J-Chr12-ZZ2 (jhxiao)/Gpt | Black |
| | | 903 | 2019 Jun. 15 | 5 | B6/J-Chr12-ZZ2 (jhxiao)/Gpt | Black |
| | | 904 | 2019 Jun. 15 | 5 | B6/J-Chr12-ZZ2 (jhxiao)/Gpt | Black |
| | | 905 | 2019 Jun. 15 | 5 | B6/J-Chr12-ZZ2 (jhxiao)/Gpt | Black |

TABLE 2B-continued

General Conditions of Mice with High Intelligence Mice and Wild-Type Mice

| Strain Numbers | Gender | Ear Number | Birth Date | Age in Weeks | Genotypes | Hair Color |
|---|---|---|---|---|---|---|
| | | 911 | 2019 Jun. 15 | 5 | B6/J-Chr12-ZZ2 (jhxiao)/Gpt | Black |
| | | 912 | 2019 Jun. 15 | 5 | B6/J-Chr12-ZZ2 (jhxiao)/Gpt | Black |
| | | 913 | 2019 Jun. 15 | 5 | B6/J-Chr12-ZZ2 (jhxiao)/Gpt | Black |
| D000765 | ♀ | 923 | 2019 Jun. 15 | 5 | B6/J-Chr12-ZZ2 (jhxiao)/Gpt | Black |
| | | 924 | 2019 Jun. 15 | 5 | B6/J-Chr12-ZZ2 (jhxiao)/Gpt | Black |
| | | 925 | 2019 Jun. 15 | 5 | B6/J-Chr12-ZZ2 (jhxiao)/Gpt | Black |
| | | 926 | 2019 Jun. 15 | 5 | B6/J-Chr12-ZZ2 (jhxiao)/Gpt | Black |
| | | 927 | 2019 Jun. 15 | 5 | B6/J-Chr12-ZZ2 (jhxiao)/Gpt | Black |
| | | 920 | 2019 Jun. 15 | 5 | B6/J-Chr12-ZZ2 (jhxiao)/Gpt | Black |
| | | 914 | 2019 Jun. 15 | 5 | B6/J-Chr12-ZZ2 (jhxiao)/Gpt | Black |
| | | 915 | 2019 Jun. 15 | 5 | B6/J-Chr12-ZZ2 (jhxiao)/Gpt | Black |
| | | 916 | 2019 Jun. 15 | 5 | B6/J-Chr12-ZZ2 (jhxiao)/Gpt | Black |
| | | 917 | 2019 Jun. 15 | 5 | B6/J-Chr12-ZZ2 (jhxiao)/Gpt | Black |

Feeding Conditions:

Animal Room Temperature: 21-25° C.; Humidity: 40%-70%; and the light and dark alternate for 12 hours.

The animals were kept on IVC cages or in isolated package plastic boxes. Feeding box specification: Length×Width×Height=300 mm×190 mm×130 mm, and each box contained at most 5 animals with the same gender.

The floor of the animal room was disinfected once a day with five different disinfectants used alternately to avoid microbial resistance. The walls, cages and ceilings were disinfected and wiped at least once a week.

The animals freely took food and drank water, which were changed once a week. The bottom box and padding were changed at least once every two weeks. If the padding was too wet due to water bottle leakage or a large amount of urine, the feeding box was changed at any moment. All the cages were cleaned and sterilized with high-pressure steam before use.

The standard SPF-grade transgenic feed of radiation laboratory mouse was purchased from Jiangsu Synergetic Pharmaceutical Biology Co., Ltd. The production unit provided the feed quality certificate for each batch of feed, and provided the third party's test report every year. The detection standard refers to the National Standard GB 14924.3-2010 Nutrient Composition of Laboratory Animal Formula Feed and GB 14924.2-2001 General Health Standard of Laboratory Animal Formula Feed.

Tap water was filtered by reverse osmosis, sterilized by high pressure vapor, and acidified for use. The appearance and bacteria indicators were tested once a month in the inventor's company, and the local water company provided the test report every year, referring to the National Standard GB5749-2006 Hygienic Standard for Drinking Water.

During the whole experiment, the animals were marked by ear numbers, and each animal had a unique animal number.

Mice (9 weeks old) began to undergo the opening field test.

Example 2 Open Field Test

Test Procedures:

1. The mice were transferred to the test room and kept undisturbed for at least 30 min prior to the detection.

2. It was ensured that the light conditions met the requirements (150-200 Lux) and the instrument operated normally.

3. The computer was turned on, the room's daily lighting was turned off, and the video recording software was run. The recording button was clicked, while the timing was started. At the time of 15 s, 30 s, 45 s, 60 s, 75 s, 90 s, 105 s and 120 s, a mouse was placed into the opening spaces No. 1, No. 2, No. 3, No. 4, No. 5, No. 6, No. 7 and No. 8, respectively, ensuring that the data were begun to be recorded just after each mouse was placed so as to ensure the consistency of the original data. The mice were placed in the direction of the midpoint of one side edge area facing the wall, and allowed to explore the opening space freely. After the mice were placed, the experimenters left the detection room (away from the mouse's line of sight).

4. After 20 min, the mice were removed, and the mouse number corresponding to each space was recorded. The mice were placed back into the original cage. If there were undetected mice in the original cage, the detected mice were placed into the spare cage, and subsequently transferred back to the original cage after all the mice were detected.

5. The excreta were cleaned out of the opening area. The entire area was wiped and dried for use in the detection of the next batch of mice.

6. The recorded data were analyzed to calculate the activity of mice in different areas every 5 min.

7. By post-detection analysis, wherein each opening space was divided into a central region and a boundary area, wherein the boundary area had a width of 8 cm away from the wall, and the central region included 40% of the total area.

Test Results:
The test results are shown in Tables 3A-3B:

TABLE 3A

| | | Results of Open Field Test | | | |
|---|---|---|---|---|---|
| | | Movement Distance (mm) | | Speed (mm/s) | Duration proportion % |
| Strain | Number | Total Area 0-20 min | Central Region 0-20 min | Total Area 0-20 min | Central Region 0-20 min |
| B6J♂ | 646 | 51317.09 | 3516.67 | 42.81 | 4.4 |
| | 643 | 51166.90 | 4440.35 | 42.68 | 5.5 |
| | 648 | 52094.59 | 3848.48 | 43.46 | 4.1 |
| | 647 | 64196.82 | 4900.37 | 53.55 | 4.8 |
| | 649 | 36319.58 | 3205.02 | 30.30 | 5.9 |
| | 698 | 38900.93 | 3034.75 | 32.45 | 7.2 |
| | 699 | 57606.71 | 3567.57 | 48.05 | 3.3 |
| | 696 | 66887.66 | 6073.94 | 55.80 | 7.1 |
| | 697 | 38892.24 | 1397.15 | 32.44 | 1.9 |
| | 695 | 34330.72 | 2244.99 | 28.64 | 2.2 |
| Average value | | 49171.324 | 3622.929 | 41.018 | 4.64 |
| D000758♂ | 170 | 35729.50 | 2317.33 | 29.80 | 2.7 |
| | 171 | 49512.75 | 1116.94 | 41.30 | 0.8 |
| | 172 | 41624.86 | 2063.21 | 34.72 | 1.8 |
| | 173 | 45045.84 | 4695.98 | 37.58 | 5.9 |
| | 137 | 37802.50 | 4107.42 | 31.53 | 4.8 |
| | 138 | 44009.15 | 3091.52 | 36.71 | 3.5 |
| | 139 | 48996.07 | 4007.09 | 40.87 | 4.1 |
| Average value | | 43245.81 | 3057.07 | 36.07285714 | 3.371428571 |
| P value (vs. B6 ♂) | | 0.18003 | 0.39416 | 0.17987 | 0.17381 |

| | | Movement Distance (mm) | | Speed (mm/s) | Duration proportion % |
|---|---|---|---|---|---|
| Strain | Number Total Area | Total Area 0-20 min | Central Region 0-20 min | Total Area 0-20 min | Central Region 0-20 min |
| B6J♀ | 620 | 88273.07 | 1753.09 | 73.63 | 1.7 |
| | 622 | 64804.21 | 3202.96 | 54.06 | 5.3 |
| | 623 | 62790.69 | 3878.36 | 52.38 | 4.3 |
| | 624 | 54237.88 | 4675.2 | 45.24 | 4.3 |
| | 644 | 42414.88 | 250.57 | 35.38 | 0.5 |
| | 665 | 44223.30 | 840.16 | 36.89 | 0.5 |
| | 666 | 59599.78 | 1096.21 | 49.72 | 1.6 |
| | 667 | 64154.90 | 496.93 | 53.52 | 0.7 |
| | 668 | 37569.82 | 1806.2 | 31.34 | 2.0 |
| | 669 | 49498.40 | 2425.39 | 41.29 | 2.7 |
| Average value | | 56756.693 | 2042.507 | 47.345 | 2.36 |
| D000758♀ | 164 | 63934.76 | 4404.35 | 53.33 | 5.9 |
| | 165 | 60020.52 | 5224.91 | 50.07 | 5.2 |
| | 166 | 54121.98 | 3136.93 | 45.15 | 2.8 |
| | 167 | 49513.57 | 4888.32 | 41.30 | 4.8 |
| | 156 | 50922.72 | 2923.41 | 42.48 | 2.5 |
| | 162 | 28007.74 | 0.0 | 23.36 | 0.0 |
| | 163 | 35767.71 | 1628.23 | 29.84 | 3.0 |
| Average value | | 48898.42857 | 3172.307143 | 40.79 | 3.457142857 |
| P value (vs. B6♀) | | 0.26189 | 0.21152 | 0.26190 | 0.26540 |

TABLE 3B

Results of Open Field Test

| Strain | Number | Movement Distance (mm) | | Speed (mm/s) | Duration proportion % |
| --- | --- | --- | --- | --- | --- |
| | | Total Area 0-20 min | Central Region 0-20 min | Total Area 0-20 min | Central Region 0-20 min |
| B6♂ | 145 | 50715.34 | 4765.89 | 42.31 | 7.60 |
| | 146 | 62756.52 | 6287.55 | 52.35 | 6.20 |
| | 147 | 55252.13 | 4730.07 | 46.09 | 4.40 |
| | 148 | 44486.60 | 3617.35 | 37.11 | 6.30 |
| | 149 | 52652.10 | 4194.14 | 43.92 | 5.40 |
| | 190 | 47945.19 | 3397.32 | 39.99 | 3.50 |
| | 191 | 63329.07 | 4510.70 | 52.83 | 4.10 |
| | 192 | 69486.30 | 6495.72 | 57.96 | 6.00 |
| | 193 | 53173.19 | 2308.90 | 44.36 | 2.80 |
| | 194 | 55395.86 | 5451.35 | 46.21 | 6.80 |
| | Average value | 55519.23 | 4575.899 | 46.313 | 5.31 |
| D000765♂ | 900 | 41414.92 | 2689.47 | 34.55 | 3.20 |
| | 910 | 35268.38 | 2644.05 | 29.42 | 4.60 |
| | 901 | 42271.14 | 1738.97 | 35.26 | 1.90 |
| | 902 | 40493.84 | 3010.07 | 33.78 | 4.50 |
| | 903 | 50728.40 | 2817.14 | 42.32 | 3.70 |
| | 904 | 39458.12 | 1768.35 | 32.91 | 2.40 |
| | 905 | 39019.34 | 2543.12 | 32.55 | 2.70 |
| | 911 | 40955.26 | 3347.31 | 34.16 | 7.90 |
| | 912 | 41489.59 | 2356.68 | 34.61 | 2.00 |
| | 913 | 50020.79 | 3885.07 | 41.73 | 4.20 |
| | Average value | 42111.978 | 2680.023 | 35.129 | 3.71 |
| | P value (vs. B6 ♂) | 0.00027 | 0.00111 | 0.00027 | 0.04596 |

| Strain | Number Total Area | Movement Distance (mm) | | Speed (mm/s) | Duration proportion % |
| --- | --- | --- | --- | --- | --- |
| | | Total Area 0-20 min | Central Region 0-20 min | Total Area 0-20 min | Central Region 0-20 min |
| B6♀ | 918 | 49959.89 | 3903.62 | 41.67 | 5.40 |
| | 195 | 68733.79 | 4330.63 | 57.34 | 4.40 |
| | 196 | 68904.42 | 4378.46 | 57.48 | 4.60 |
| | 928 | 56055.86 | 6331.70 | 46.76 | 9.50 |
| | 919 | 38892.82 | 1931.42 | 32.44 | 2.50 |
| | 906 | 63874.09 | 4861.97 | 53.28 | 5.40 |
| | 907 | 75460.22 | 2426.39 | 62.95 | 1.60 |
| | 908 | 54101.48 | 5874.29 | 45.13 | 11.10 |
| | 909 | 59533.09 | 4226.80 | 49.66 | 4.40 |
| | 929 | 93586.71 | 5080.14 | 78.07 | 4.00 |
| | Average value | 62910.237 | 4334.542 | 52.478 | 5.29 |
| D000765♀ | 927 | 22753.15 | 439.00 | 18.98 | 0.50 |
| | 924 | 35306.20 | 2350.19 | 29.45 | 7.90 |
| | 925 | 52461.94 | 3182.70 | 43.76 | 5.20 |
| | 926 | 42050.05 | 1991.73 | 35.08 | 1.80 |
| | 927 | 64524.87 | 5137.87 | 53.82 | 6.40 |
| | 920 | 44600.75 | 2675.10 | 37.20 | 2.70 |
| | 914 | 44941.55 | 1790.40 | 37.49 | 2.70 |
| | 915 | 35553.27 | 2061.93 | 29.66 | 2.20 |
| | 916 | 53861.29 | 3915.78 | 44.93 | 4.40 |
| | 917 | 39469.69 | 1785.85 | 32.92 | 2.10 |
| | Average value | 43552.276 | 2533.055 | 36.329 | 3.59 |
| | P value (vs. B6 ♀) | 0.00511 | 0.00735 | 0.00511 | 0.16696 |

The test results are shown in FIG. 1 to FIG. 4. Of those, FIG. 1 to FIG. 4 show the conditions of the open field tests of D000758 male mouse, D000758 female mouse, D000765 male mouse and D000765 female mouse, respectively, wherein each graph is compared with the control mouse (B6, all located on the left of the bar graph). The results show:

As compared with the control mouse, the movement distance and speed of D000758 male mouse does not exhibit a significant change in all the areas. As compared with the control mouse, the movement distance and speed of D000758 female mouse is significantly less than those of the control in all the areas with a significant difference (*P<0.05).

As compared with the control mouse, the movement distance and speed of D000765 male mouse is significantly reduced in all the areas and the central region. As compared with the control mouse, the movement distance and speed of D000765 female mouse is significantly less than those of the control in all the areas with a significant difference (*P<0.05), and the distance in the central region is significantly less than that of the control female mouse.

Example 3 Sucrose Preference Test

Test Procedures:

Preparation of sucrose: An 8% aqueous sucrose solution was formulated with distilled water.

Sucrose preference test: including two parts, that is, the adaptation training part and the test part:

Adaption training: adaption training was carried out before modeling. During the training, the laboratory mice were exposed in a metabolism cage containing a bottle of clear water and a bottle of 8% aqueous sucrose solution for 2 hours of adaption. After 1 hour, the positions of the two bottles of water were changed, and the adaption lasted for 3 days.

Test: the mice were subject to water deprivation without fasting for 12 hours. Before the test, one bottle of clear water and one bottle of 8% aqueous sucrose solution were weighed. During the test, the laboratory mice were exposed to a metabolism cage containing one bottle of clear water and one bottle of 8% aqueous sucrose solution. During the test, the positions of the two bottles were not changed. After two hours, the bottles were removed and weighed, and the consumptions of clear water and aqueous sucrose were recorded.

The consumption rate of the aqueous sucrose solution is calculated as: sucrose preference index %=consumption of aqueous sucrose solution/(consumption of aqueous sucrose solution+consumption of pure water)×100%.

Test Results:

The test results are shown in Tables 4A-4B:

TABLE 4A

Results of Sucrose Preference Test

| | Animal ID | Distributed Amount | Residual Amount Sucrose (g) | Drinking Amount in 2 Hours | Distributed Amount | Residual Amount Water (g) | Drinking Amount in 2 Hours | Sucrose Preference Index (%) |
|---|---|---|---|---|---|---|---|---|
| ♂B6 | 646 | 68.1 | 65.4 | 2.7 | 79.2 | 78.3 | 0.9 | 75.0 |
| | 647 | 66.7 | 63.9 | 2.8 | 88.9 | 88.3 | 0.6 | 82.4 |
| | 648 | 67.8 | 65.6 | 2.2 | 86.2 | 85.5 | 0.7 | 75.9 |
| | 649 | 68.9 | 66.5 | 2.4 | 84.1 | 83.2 | 0.9 | 72.7 |
| | 643 | 66.3 | 63.8 | 2.5 | 74.7 | 73.7 | 1.0 | 71.4 |
| | 695 | 65.3 | 62.9 | 2.4 | 77.5 | 76.7 | 0.8 | 75.0 |
| | 696 | 65.3 | 63.1 | 2.2 | 73 | 72.5 | 0.5 | 81.5 |
| | 697 | 69.0 | 66.4 | 2.6 | 75.2 | 74.7 | 0.5 | 83.9 |
| | 698 | 65.6 | 62.2 | 3.4 | 75.1 | 74.4 | 0.7 | 82.9 |
| | 699 | 67.2 | 64.6 | 2.6 | 66.3 | 65.7 | 0.6 | 81.3 |
| | Average value | 67.02 | 64.44 | 2.58 | 78.02 | 77.3 | 0.72 | 78.2 |
| ♂D000758 | 170 | 67.9 | 65.7 | 2.2 | 71.1 | 70.7 | 0.4 | 84.6 |
| | 171 | 63.3 | 62.0 | 1.3 | 80.1 | 79.4 | 0.7 | 65.0 |
| | 172 | 69.2 | 67.1 | 2.1 | 63.7 | 63.1 | 0.6 | 77.8 |
| | 173 | 66.8 | 65.1 | 1.7 | 76.9 | 76.4 | 0.5 | 77.3 |
| | 137 | 68.5 | 66.3 | 2.2 | 72.5 | 71.8 | 0.7 | 75.9 |
| | 138 | 67.6 | 65.3 | 2.3 | 76.2 | 75.5 | 0.7 | 76.7 |
| | 139 | 68.4 | 66.8 | 1.6 | 76.4 | 75.6 | 0.8 | 66.7 |
| | Average value | 67.4 | 65.5 | 1.9 | 73.8 | 73.2 | 0.63 | 75.3 |
| | P value (vs. B6 ♂) | 0.680216 | 0.221301 | 0.003068 | 0.177914 | 0.184353 | 0.248452 | 0.284488 |
| B6♀ | 620 | 65.6 | 63.4 | 2.2 | 63.8 | 63.3 | 0.5 | 81.5 |
| | 622 | 70.3 | 68.5 | 1.8 | 73.0 | 72.5 | 0.5 | 78.3 |
| | 623 | 70.5 | 67.6 | 2.9 | 76.7 | 76.2 | 0.5 | 85.3 |
| | 624 | 70.5 | 68.4 | 2.1 | 77.2 | 76.4 | 0.8 | 72.4 |
| | 644 | 74.0 | 72.0 | 2 | 77.1 | 76.6 | 0.5 | 80.0 |
| | 665 | 68.5 | 66.6 | 1.9 | 81.7 | 81.3 | 0.4 | 82.6 |
| | 666 | 70.1 | 67.0 | 3.1 | 70.5 | 69.9 | 0.6 | 83.8 |
| | 667 | 72.3 | 69.6 | 2.7 | 74.9 | 74.7 | 0.2 | 93.1 |
| | 668 | 69.7 | 68.1 | 1.6 | 76.4 | 75.8 | 0.6 | 72.7 |
| | 669 | 68.9 | 67.0 | 1.9 | 74.9 | 74.4 | 0.5 | 79.2 |
| | Average value | 70.04 | 67.82 | 2.22 | 74.62 | 74.11 | 0.51 | 81.3 |
| ♀D000758 | 164 | 65.9 | 63.6 | 2.3 | 73.7 | 73.3 | 0.4 | 85.2 |
| | 165 | 75.5 | 73.6 | 1.9 | 75.7 | 74.9 | 0.8 | 70.4 |
| | 166 | 65.6 | 62.6 | 3.0 | 73.7 | 73.3 | 0.4 | 88.2 |
| | 167 | 67.5 | 65.0 | 2.5 | 75.4 | 74.9 | 0.5 | 83.3 |
| | 156 | 67.8 | 65.1 | 2.7 | 70.8 | 70.1 | 0.7 | 79.4 |
| | 162 | 67.8 | 64.7 | 3.1 | 74.3 | 74 | 0.3 | 91.2 |
| | 163 | 63.3 | 61.6 | 1.7 | 63.3 | 62.2 | 1.1 | 60.7 |

TABLE 4A-continued

Results of Sucrose Preference Test

| | Animal ID | Distributed Amount | Residual Amount Sucrose (g) | Drinking Amount in 2 Hours | Distributed Amount | Residual Amount Water (g) | Drinking Amount in 2 Hours | Sucrose Preference Index (%) |
|---|---|---|---|---|---|---|---|---|
| Average value | | 67.63 | 65.17 | 2.457142857 | 72.41 | 71.81 | 0.60 | 80.4 |
| P value (vs. B6 ♀) | | 0.168779 | 0.143170 | 0.371253 | 0.339623 | 0.334102 | 0.463681 | 0.810965 |

TABLE 4B

Results of Sucrose Preference Test

| | Animal ID | Distributed Amount | Residual Amount Sucrose (g) | Drinking Amount in 2 Hours | Distributed Amount | Residual Amount Water (g) | Drinking Amount in 2 Horns | Sucrose Preference Index (%) |
|---|---|---|---|---|---|---|---|---|
| ♂ B6 | 145 | 66.0 | 63.5 | 2.5 | 81.7 | 80.9 | 0.8 | 75.76 |
| | 146 | 68.2 | 66.1 | 2.1 | 78.3 | 77.5 | 0.8 | 72.41 |
| | 147 | 75.6 | 73.5 | 2.1 | 76.9 | 76.1 | 0.8 | 72.41 |
| | 148 | 72.3 | 69.4 | 2.9 | 75.4 | 74.9 | 0.5 | 85.29 |
| | 149 | 75.2 | 72.6 | 2.6 | 81.5 | 80.7 | 0.8 | 76.47 |
| | 190 | 70.2 | 67.7 | 2.5 | 78.6 | 77.8 | 0.8 | 75.76 |
| | 191 | 71.6 | 69.1 | 2.5 | 73.9 | 72.9 | 1.0 | 71.43 |
| | 192 | 77.4 | 73.8 | 3.6 | 80.3 | 79.1 | 1.2 | 75.00 |
| | 193 | 72.9 | 70.8 | 2.1 | 81.4 | 80.9 | 0.5 | 80.77 |
| | 194 | 69.5 | 67.4 | 2.1 | 91.2 | 90.7 | 0.5 | 80.77 |
| Average value | | 71.89 | 69.39 | 2.5 | 79.92 | 79.15 | 0.77 | 76.61 |
| ♂ D000765 | 900 | 68.9 | 66.9 | 2 | 84.8 | 84.5 | 0.3 | 86.96 |
| | 910 | 69.6 | 68.1 | 1.5 | 83.7 | 83.3 | 0.4 | 78.95 |
| | 901 | 70.4 | 68.7 | 1.7 | 80.1 | 79.7 | 0.4 | 80.95 |
| | 902 | 69.5 | 67.5 | 2 | 76.5 | 75.8 | 0.7 | 74.07 |
| | 903 | 63.1 | 61.6 | 1.5 | 76.7 | 75.9 | 0.8 | 65.22 |
| | 904 | 71.2 | 69.5 | 1.7 | 85.8 | 85.1 | 0.7 | 70.83 |
| | 905 | 70.8 | 68.7 | 2.1 | 77.6 | 77.2 | 0.4 | 84.00 |
| | 911 | 65.5 | 63.5 | 2 | 80.1 | 78.7 | 1.4 | 58.82 |
| | 912 | 70.1 | 68.6 | 1.5 | 74.4 | 74.0 | 0.4 | 78.95 |
| | 913 | 71.5 | 70.0 | 1.5 | 75.1 | 74.8 | 0.3 | 83.33 |
| Average value | | 69.1 | 67.3 | 1.8 | 80.7 | 80.2 | 0.5 | 77.3 |
| P value (vs. B6 ♂) | | 0.08556 | 0.16985 | 0.00118 | 0.70543 | 0.63187 | 0.03486 | 0.83844 |
| B6 ♀ | 918 | 70.7 | 68.9 | 1.8 | 85.6 | 84.8 | 0.8 | 69.23 |
| | 195 | 72.5 | 69.6 | 2.9 | 84.6 | 83.7 | 0.9 | 76.32 |
| | 196 | 71.8 | 70.4 | 1.4 | 80.6 | 80.1 | 0.5 | 73.68 |
| | 928 | 71.9 | 69.5 | 2.4 | 77.0 | 76.5 | 0.5 | 82.76 |
| | 919 | 65.2 | 63.1 | 2.1 | 77.6 | 76.7 | 0.9 | 70.00 |
| | 906 | 73.3 | 71.2 | 2.1 | 86.6 | 85.8 | 0.8 | 72.41 |
| | 907 | 72.2 | 70.8 | 1.4 | 78.4 | 77.6 | 0.8 | 63.64 |
| | 908 | 68.3 | 65.5 | 2.8 | 80.5 | 80.1 | 0.4 | 87.50 |
| | 909 | 72.2 | 70.1 | 2.1 | 75.3 | 74.4 | 0.9 | 70.00 |
| | 929 | 72.4 | 70.5 | 1.9 | 75.7 | 75.1 | 0.6 | 76.00 |
| Average value | | 71.05 | 68.96 | 2.09 | 80.19 | 79.48 | 0.71 | 74.15 |
| ♀ D000765 | 927 | 66.1 | 64.2 | 1.9 | 76.8 | 76.1 | 0.7 | 73.08 |
| | 924 | 63.5 | 62.3 | 1.2 | 85.1 | 84.5 | 0.6 | 66.67 |
| | 925 | 67.2 | 65.2 | 2 | 84.1 | 83.7 | 0.4 | 83.33 |
| | 926 | 62.9 | 60.6 | 2.3 | 82.4 | 82.3 | 0.1 | 95.83 |
| | 927 | 67.3 | 65.8 | 1.5 | 77.2 | 76.7 | 0.5 | 75.00 |
| | 920 | 66.0 | 64.0 | 2 | 80 | 79.6 | 0.4 | 83.33 |
| | 914 | 65.2 | 63.5 | 1.7 | 76.1 | 75.5 | 0.6 | 73.91 |
| | 915 | 66.8 | 64.4 | 2.4 | 71.1 | 70.1 | 1.0 | 70.59 |
| | 916 | 66.2 | 64.4 | 1.8 | 74.7 | 74 | 0.7 | 72.00 |
| | 917 | 65.0 | 62.7 | 2.3 | 82.2 | 81 | 1.2 | 65.71 |
| Average value | | 65.46 | 63.66 | 1.80 | 80.24 | 79.77 | 0.47 | 75.95 |
| P value (vs. B6 ♀) | | 0.000028 | 0.000069 | 0.382131 | 0.536743 | 0.571354 | 0.448840 | 0.627939 |

Figure 5:
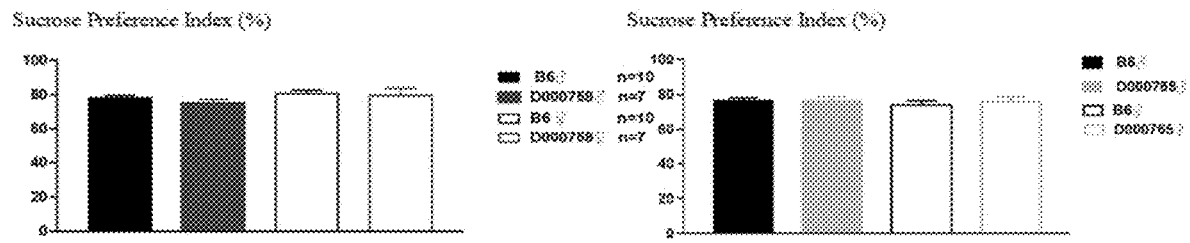
FIG. 5 shows the result of the sucrose preference test of the mouse with high intelligence level of the present application.

Test Results are shown in FIG. 5. The bar graph from the left was sequentially B6 male mouse, D000758 male mouse, B6 female mouse and D000758 female mouse, or from the left was sequentially B6 male mouse, D000765 male mouse, B6 female mouse and D000765 female mouse.

The results show that as compared with the control mouse, D000758 male and female mice do not exhibit a significant difference in sucrose preference. As compared with the control mouse, D000765 male and female mice do not exhibit a significant difference in sucrose preference.

Example 4 Water Maze Test

Test Procedures:

The mice were transferred to the test room and kept undisturbed for at least 30 min prior to the detection.

It was ensured that the lighting conditions meet the requirements and the instrument operates normally. The ambient temperature was 26° C., and the water temperature was 20-22° C. The water pool was dyed, and white dye was used to highlight the black mice. Colorful papers with different colors and shapes were pasted around the water pool to facilitate the identification of mice.

The computer was turned on, the room's daily lighting was turned off, and the video recording software was run. The mice were placed into the water pool, and a video was simultaneously begun to be recorded, ensuring that the data were begun to be recorded just after each mouse was placed so as to ensure the consistency of the original data. The mice were placed in a position of the midpoint of one side edge area facing the wall, and allowed to explore the platform in the water pool freely. After the mice were placed, the experimenters left the detection room (away from the mouse's line of sight).

If the mouse can find the platform successfully, let it stay on the platform for 30 s (to increase its memory time). If the mouse cannot yet find the platform after 90 s, guide it with a guide rod to the platform and let it stay for 30 s. After that, the mouse number was recorded. The mice were wiped to dry and placed back into the original cage. If there were still undetected mice in the original cage, they were placed into the spare cage, and then transferred back into the original cage after all were detected.

The operation of step 4) was repeated at the four quadrants in the water pool. The interval between time of entering in the water of each mouse was controlled around 30 min, and the acquired training lasted for 4 days.

After 4 days of the acquired training, an exploration test was performed on Day 5. The platform was removed, and the mice were placed on the opposite side of the original platform. The time lengths and times of mice entering the target quadrant were recorded as the detection index of spatial memory.

The recorded data were analyzed to calculate the activity of mice in different areas every 5 min.

Test Results:

The test results are shown in Tables 5A-5B:

TABLE 5A

Results of Water Maze Test

| Group | Animal Number | Latency of Platform | | | | Exploration Duration Proportion % | |
|---|---|---|---|---|---|---|---|
| | | Day 1 | Day 2 | Day 3 | Day 4 | 1 | 2 |
| B6 ♂ | 646 | 89.83 | 89.96 | 89.96 | 89.96 | 1.90 | 36.90 |
| | 647 | 89.88 | 68.25 | 89.96 | 82.15 | 30.40 | 15.60 |
| | 648 | 32.72 | 8.34 | 43.34 | 8.08 | 6.90 | 34.90 |
| | 649 | 28.17 | 48.95 | 4.02 | 18.89 | 10.60 | 38.30 |
| | 643 | 78.45 | 37.22 | 48.37 | 55.94 | 23.90 | 31.70 |
| | 695 | 68.68 | 89.96 | 89.96 | 89.96 | 0.00 | 0.00 |
| | 696 | 89.96 | 46.72 | 53.61 | 53.65 | 5.00 | 7.10 |
| | 697 | 89.74 | 70.76 | 89.96 | 73.63 | 0.00 | 0.00 |
| | 698 | 67.00 | 35.67 | 8.76 | 33.69 | 8.70 | 45.10 |
| | 699 | 89.96 | 59.69 | 7.13 | 38.94 | 14.90 | 22.80 |
| Average value | | 72.44 | 55.55 | 52.51 | 54.49 | 10.23 | 23.24 |
| D000758 ♂ | 170 | 70.03 | 75.32 | 26.91 | 41.44 | 23.80 | 30.90 |
| | 171 | 51.15 | 36.62 | 89.96 | 71.00 | 34.10 | 31.90 |
| | 172 | 49.17 | 71.17 | 87.47 | 34.39 | 32.10 | 47.50 |
| | 173 | 61.29 | 32.13 | 17.93 | 11.02 | 16.30 | 24.40 |
| | 137 | 89.96 | 89.63 | 89.96 | 89.96 | 14.20 | 39.60 |
| | 138 | 63.56 | 38.24 | 54.30 | 44.09 | 11.80 | 59.80 |
| | 139 | 72.79 | 41.04 | 13.34 | 34.89 | 11.00 | 25.90 |
| Average value | | 65.42 | 54.88 | 54.27 | 46.68 | 20.47 | 37.14 |
| P value (vs. B6 ♂) | | 0.458203 | 0.955667 | 0.921822 | 0.572860 | 0.054009 | 0.071130 |
| B6 ♀ | 620 | 75.74 | 67.91 | 43.46 | 41.12 | 25.40 | 26.10 |
| | 622 | 59.50 | 89.96 | 89.96 | 89.96 | 64.10 | 2.30 |
| | 623 | 89.96 | 77.42 | 57.90 | 26.65 | 20.10 | 30.80 |
| | 624 | 74.76 | 52.98 | 83.98 | 84.84 | 26.90 | 31.50 |
| | 644 | 89.79 | 89.96 | 80.32 | 88.02 | 24.40 | 19.20 |
| | 665 | 89.51 | 15.33 | 13.78 | 27.71 | 24.00 | 41.80 |
| | 666 | 48.59 | 9.88 | 12.83 | 11.62 | 21.30 | 31.30 |
| | 667 | 79.81 | 82.21 | 41.78 | 65.20 | 40.70 | 12.10 |

TABLE 5A-continued

Results of Water Maze Test

|  |  |  |  |  |  |  |  |
|---|---|---|---|---|---|---|---|
|  | 668 | 89.96 | 69.05 | 83.38 | 83.07 | 0.00 | 0.00 |
|  | 669 | 40.33 | 14.16 | 14.33 | 67.85 | 40.50 | 10.40 |
| Average value |  | 73.80 | 56.89 | 52.17 | 58.60 | 28.74 | 20.55 |
| D000758 ♀ | 164 | 31.95 | 10.61 | 30.54 | 19.54 | 13.60 | 39.80 |
|  | 165 | 48.55 | 43.47 | 62.94 | 52.23 | 32.80 | 18.50 |
|  | 166 | 89.84 | 47.86 | 17.82 | 70.00 | 19.00 | 42.10 |
|  | 167 | 69.99 | 32.85 | 8.80 | 27.83 | 33.50 | 29.40 |
|  | 156 | 46.00 | 40.21 | 45.35 | 31.93 | 16.40 | 55.40 |
|  | 162 | 30.92 | 18.28 | 23.12 | 15.94 | 9.80 | 39.70 |
|  | 163 | 68.76 | 63.38 | 12.81 | 59.02 | 6.20 | 27.30 |
| Average value |  | 55.14 | 39.68 | 35.13 | 48.60 | 20.05 | 28.32 |
| P value (vs. B6 ♀) |  | 0.090290 | 0.119385 | 0.077454 | 0.137851 | 0.155641 | 0.028182 |

| Group | Animal Number | Exploration | | | | Time for Quadrant 2 (s) |
|---|---|---|---|---|---|---|
|  |  | Duration Proportion % | | Distance (mm) | Speed (mm/s) |  |
|  |  | 3 | 4 |  |  |  |
| B6 ♂ | 646 | 35.80 | 25.30 | 4981.59 | 56.12 | 33.20 |
|  | 647 | 25.80 | 28.10 | 8049.33 | 90.69 | 14.04 |
|  | 648 | 40.80 | 16.90 | 17725.42 | 199.70 | 31.36 |
|  | 649 | 13.00 | 37.30 | 16567.34 | 186.65 | 34.48 |
|  | 643 | 30.20 | 13.60 | 13371.32 | 150.65 | 28.56 |
|  | 695 | 3.70 | 96.30 | 2957.99 | 33.33 | 0.00 |
|  | 696 | 67.90 | 20.00 | 9831.90 | 110.77 | 6.40 |
|  | 697 | 37.40 | 62.60 | 2620.83 | 29.53 | 0.00 |
|  | 698 | 28.80 | 16.10 | 20353.55 | 229.31 | 40.60 |
|  | 699 | 6.20 | 55.80 | 12838.79 | 144.65 | 20.48 |
| Average value |  | 28.96 | 37.20 | 10929.81 | 123.14 | 20.91 |
|  | 170 | 31.30 | 13.50 | 17603.29 | 198.32 | 27.80 |
|  | 171 | 3.60 | 30.30 | 7265.38 | 81.85 | 28.72 |
|  | 172 | 12.50 | 7.90 | 20058.08 | 225.98 | 42.72 |
| D000758 ♂ | 173 | 29.40 | 29.10 | 20379.19 | 229.60 | 21.92 |
|  | 137 | 19.20 | 27.00 | 13915.03 | 156.77 | 35.64 |
|  | 138 | 2.20 | 25.20 | 10761.12 | 121.24 | 53.84 |
|  | 139 | 29.30 | 33.40 | 14693.12 | 165.54 | 23.32 |
| Average value |  | 18.21 | 23.77 | 14953.60 | 168.47 | 33.42 |
| P value (vs. B6 ♂) |  | 0.176897 | 0.168785 | 0.156727 | 0.156743 | 0.071226 |
| B6 ♀ | 620 | 20.10 | 27.80 | 21620.13 | 243.58 | 23.52 |
|  | 622 | 14.50 | 19.20 | 5463.38 | 61.55 | 2.04 |
|  | 623 | 11.70 | 36.50 | 16021.65 | 180.51 | 27.68 |
|  | 624 | 11.90 | 29.70 | 10657.25 | 120.07 | 28.36 |
|  | 644 | 10.30 | 46.10 | 15284.65 | 172.20 | 17.28 |
|  | 665 | 11.80 | 22.10 | 18268.97 | 205.82 | 37.60 |
|  | 666 | 26.00 | 20.30 | 20247.64 | 228.12 | 28.12 |
|  | 667 | 13.20 | 33.80 | 10739.78 | 121.00 | 10.92 |
|  | 668 | 75.00 | 25.00 | 2286.12 | 25.76 | 0.00 |
|  | 669 | 14.80 | 34.40 | 17914.05 | 201.83 | 9.36 |
| Average value |  | 20.93 | 29.49 | 13850.36 | 156.04 | 18.49 |
| D000758 ♀ | 164 | 21.20 | 24.40 | 20957.69 | 236.12 | 35.80 |
|  | 165 | 6.00 | 42.70 | 13415.06 | 151.14 | 16.64 |
|  | 166 | 8.60 | 30.10 | 16549.53 | 186.45 | 37.88 |
|  | 167 | 8.40 | 28.30 | 16338.17 | 184.07 | 26.48 |
|  | 156 | 16.80 | 9.50 | 16990.73 | 191.42 | 49.88 |
|  | 162 | 27.00 | 22.80 | 19145.64 | 215.70 | 35.68 |
|  | 163 | 38.70 | 27.40 | 16258.66 | 183.18 | 24.56 |
| Average value |  | 23.74 | 27.41 | 16688.23 | 188.02 | 30.68 |
| P value (vs. B6 ♀) |  | 0.716585 | 0.521271 | 0.168325 | 0.168336 | 0.028187 |

TABLE 5B

| | | Results of Water Maze Test | | | | | |
|---|---|---|---|---|---|---|---|
| | | | | | | Exploration Duration Proportion % | |
| | Animal | Platform Delay | | | | | |
| Group | Number | Day 1 | Day 2 | Day 3 | Day 4 | 1 | 2 |
| B6♂ | 145 | 7.65 | 28.29 | 35.57 | 71.92 | 12.90 | 27.90 |
| | 146 | 35.02 | 84.56 | 18.65 | 47.37 | 17.30 | 28.90 |
| | 147 | 89.96 | 68.08 | 89.96 | 68.66 | 0.00 | 0.00 |
| | 148 | 69.66 | 68.63 | 82.37 | 48.84 | 22.30 | 62.80 |
| | 149 | 74.91 | 8.36 | 32.74 | 50.06 | 8.00 | 26.30 |
| | 190 | 89.61 | 89.96 | 89.96 | 89.79 | 0.00 | 28.40 |
| | 191 | 72.65 | 38.92 | 73.48 | 89.79 | 25.40 | 32.50 |
| | 192 | 89.96 | 89.96 | 80.32 | 87.12 | 14.80 | 48.10 |
| | 193 | 89.96 | 89.96 | 60.09 | 80.31 | 13.80 | 40.60 |
| | 194 | 89.83 | 89.96 | 89.96 | 38.88 | 4.20 | 34.50 |
| Average value | | 70.921 | 65.668 | 65.31 | 67.274 | 11.87 | 33 |
| D000765♂ | 900 | 21.66 | 46.24 | 19.89 | 14.57 | 13.30 | 46.60 |
| | 910 | 39.90 | 26.60 | 3.08 | 31.92 | 28.90 | 37.90 |
| | 901 | 73.25 | 23.74 | 16.53 | 7.33 | 22.30 | 43.80 |
| | 902 | 53.61 | 58.04 | 46.20 | 13.03 | 40.80 | 37.30 |
| | 903 | 51.18 | 61.35 | 27.88 | 28.74 | 17.30 | 43.70 |
| | 904 | 57.22 | 11.01 | 35.58 | 4.33 | 26.60 | 50.20 |
| | 905 | 19.39 | 12.15 | 24.24 | 8.42 | 18.90 | 31.00 |
| | 911 | 58.63 | 34.62 | 9.34 | 19.07 | 15.10 | 69.00 |
| | 912 | 28.75 | 10.05 | 5.12 | 9.47 | 43.10 | 39.10 |
| | 913 | 63.50 | 32.75 | 6.53 | 7.33 | 12.60 | 48.00 |
| Average value | | 46.709 | 31.655 | 19.439 | 14.421 | 23.89 | 44.66 |
| P value (vs. B6 ♂) | | 0.0371704 | 0.0082849 | 0.0003300 | 0.0000034 | 0.0146404 | 0.0742431 |
| | 918 | 89.80 | 37.36 | 24.62 | 30.17 | 17.20 | 20.50 |
| | 195 | 68.41 | 50.11 | 18.36 | 36.32 | 15.40 | 37.30 |
| | 196 | 67.69 | 67.47 | 68.29 | 82.00 | 18.10 | 28.70 |
| | 928 | 89.96 | 31.57 | 58.78 | 43.59 | 15.10 | 26.40 |
| | 919 | 54.97 | 34.09 | 42.74 | 30.06 | 16.30 | 21.30 |
| | 906 | 71.24 | 73.49 | 22.74 | 59.56 | 20.10 | 19.90 |
| | 907 | 56.86 | 56.76 | 37.51 | 38.18 | 13.80 | 21.50 |
| | 908 | 89.96 | 56.80 | 54.09 | 46.04 | 17.60 | 27.90 |
| | 909 | 89.96 | 89.96 | 79.55 | 17.10 | 22.00 | 43.60 |
| | 929 | 89.74 | 67.47 | 20.54 | 25.44 | 22.30 | 46.10 |
| Average value | | 76.859 | 56.508 | 42.722 | 40.846 | 17.79 | 29.32 |
| D000765♀ | 927 | 28.11 | 9.42 | 14.13 | 9.41 | 16.60 | 47.50 |
| | 924 | 31.92 | 21.32 | 5.99 | 6.55 | 25.80 | 28.80 |
| | 925 | 89.96 | 41.12 | 42.57 | 31.49 | 20.90 | 34.40 |
| | 926 | 42.71 | 45.20 | 8.80 | 3.86 | 13.70 | 53.40 |
| | 927 | 72.92 | 68.34 | 12.63 | 7.66 | 18.80 | 26.00 |
| | 920 | 59.15 | 21.68 | 31.12 | 16.90 | 27.40 | 36.10 |
| | 914 | 34.09 | 31.57 | 24.77 | 38.75 | 8.00 | 42.40 |
| | 915 | 46.92 | 19.94 | 2.85 | 15.82 | 35.40 | 16.10 |
| | 916 | 57.32 | 11.42 | 10.46 | 17.71 | 17.10 | 36.40 |
| | 917 | 66.60 | 27.98 | 13.01 | 36.86 | 18.40 | 28.00 |
| Average value | | 52.97 | 29.799 | 16.633 | 18.501 | 20.21 | 34.91 |
| P value (vs. B6 ♀) | | 0.0072673 | 0.0043210 | 0.0051203 | 0.0066371 | 0.3711929 | 0.2433076 |

| | | Exploration | | | |
|---|---|---|---|---|---|
| | Animal | Duration Proportion % | | Distance | Speed | Time for Quadrant |
| Group | Number | 3 | 4 | (mm) | (mm/s) | 2 (s) |
| B6♂ | 145 | 28.70 | 30.50 | 16368.34 | 184.41 | 25.08 |
| | 146 | 41.70 | 11.90 | 18255.29 | 205.67 | 26.04 |
| | 147 | 44.60 | 55.40 | 1485.18 | 16.73 | 0.00 |
| | 148 | 12.90 | 2.00 | 13176.79 | 148.45 | 56.48 |
| | 149 | 51.10 | 14.20 | 10787.45 | 121.54 | 23.68 |
| | 190 | 53.40 | 18.10 | 2165.50 | 24.40 | 25.56 |
| | 191 | 18.30 | 23.10 | 18479.79 | 208.20 | 29.20 |
| | 192 | 23.30 | 13.50 | 9960.83 | 112.22 | 43.24 |

TABLE 5B-continued

Results of Water Maze Test

| | | | | | | |
|---|---|---|---|---|---|---|
| | 193 | 25.20 | 19.50 | 9603.78 | 108.20 | 36.52 |
| | 194 | 27.80 | 33.40 | 7437.20 | 83.79 | 31.04 |
| Average value | | 32.7 | 22.16 | 10772.015 | 121.361 | 29.684 |
| D000765♂ | 900 | 26.00 | 12.10 | 17990.46 | 202.69 | 41.88 |
| | 910 | 11.30 | 21.10 | 15959.91 | 179.81 | 34.12 |
| | 901 | 17.90 | 13.30 | 17389.91 | 195.92 | 39.36 |
| | 902 | 7.60 | 11.70 | 15186.04 | 171.09 | 33.52 |
| | 903 | 26.10 | 12.90 | 19796.16 | 223.03 | 39.28 |
| | 904 | 10.40 | 11.40 | 15193.47 | 171.17 | 45.20 |
| | 905 | 17.00 | 33.10 | 19247.04 | 216.84 | 27.88 |
| | 911 | 13.10 | 0.00 | 16813.14 | 189.42 | 62.04 |
| | 912 | 2.70 | 14.10 | 18563.93 | 209.15 | 35.20 |
| | 913 | 21.70 | 15.10 | 18299.20 | 206.16 | 43.16 |
| Average value | | 15.38 | 14.48 | 17443.926 | 196.528 | 40.164 |
| P value (vs. B6 ♂) | | 0.0041867 | 0.1748912 | 0.0066647 | 0.0066651 | 0.0743229 |
| | 918 | 23.10 | 39.20 | 7270.05 | 81.91 | 18.40 |
| | 195 | 27.10 | 20.20 | 16960.87 | 191.09 | 33.52 |
| | 196 | 22.80 | 30.30 | 20277.39 | 228.45 | 25.84 |
| | 928 | 27.10 | 31.50 | 15809.33 | 178.11 | 23.72 |
| | 919 | 26.00 | 35.50 | 16353.41 | 184.24 | 19.12 |
| | 906 | 29.20 | 30.50 | 14081.41 | 158.65 | 17.88 |
| | 907 | 19.20 | 45.00 | 12912.00 | 145.47 | 19.36 |
| | 908 | 17.40 | 37.10 | 7258.27 | 81.77 | 25.08 |
| | 909 | 14.90 | 18.80 | 16478.59 | 185.65 | 39.20 |
| | 929 | 19.80 | 11.40 | 18244.21 | 205.55 | 41.44 |
| Average value | | 22.66 | 29.95 | 14564.553 | 164.089 | 26.356 |
| D000765♀ | 927 | 24.60 | 8.70 | 17743.95 | 199.91 | 42.72 |
| | 924 | 23.00 | 22.30 | 22594.63 | 254.56 | 25.92 |
| | 925 | 21.00 | 22.10 | 19668.25 | 221.59 | 30.92 |
| | 926 | 23.20 | 8.90 | 18931.33 | 213.29 | 48.04 |
| | 927 | 16.80 | 37.50 | 15648.02 | 176.30 | 23.40 |
| | 920 | 26.40 | 8.30 | 17476.84 | 196.90 | 32.44 |
| | 914 | 23.50 | 26.10 | 14145.12 | 159.36 | 38.16 |
| | 915 | 20.20 | 26.90 | 19454.50 | 219.18 | 14.52 |
| | 916 | 25.80 | 19.80 | 21715.90 | 244.66 | 32.76 |
| | 917 | 29.80 | 21.90 | 22547.66 | 254.03 | 25.16 |
| Average value | | 23.43 | 20.25 | 18992.62 | 213.978 | 31.404 |
| P value (vs. B6 ♀) | | 0.6874879 | 0.0413548 | 0.0161262 | 0.0161250 | 0.2413410 |

Figure 6:
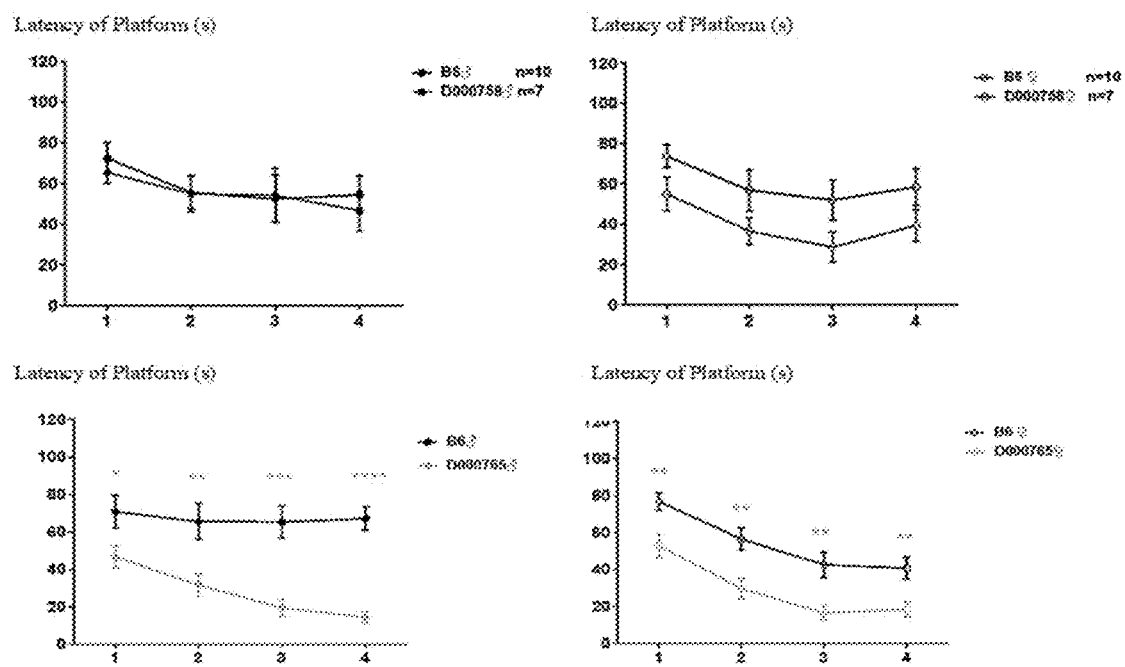
FIG. 6 to FIG. 8 show the results of the water maze test of the mouse with high intelligence level of the present application.

Test Results are shown in FIG. 6. The results show that during the acquired training, the latency of platform of D000758 male and female mice is not significantly different from that of the control mouse; and during the acquired training, the latency of platform of D000765 male and female mice is significantly less than that of the control mouse.

Figure 7:
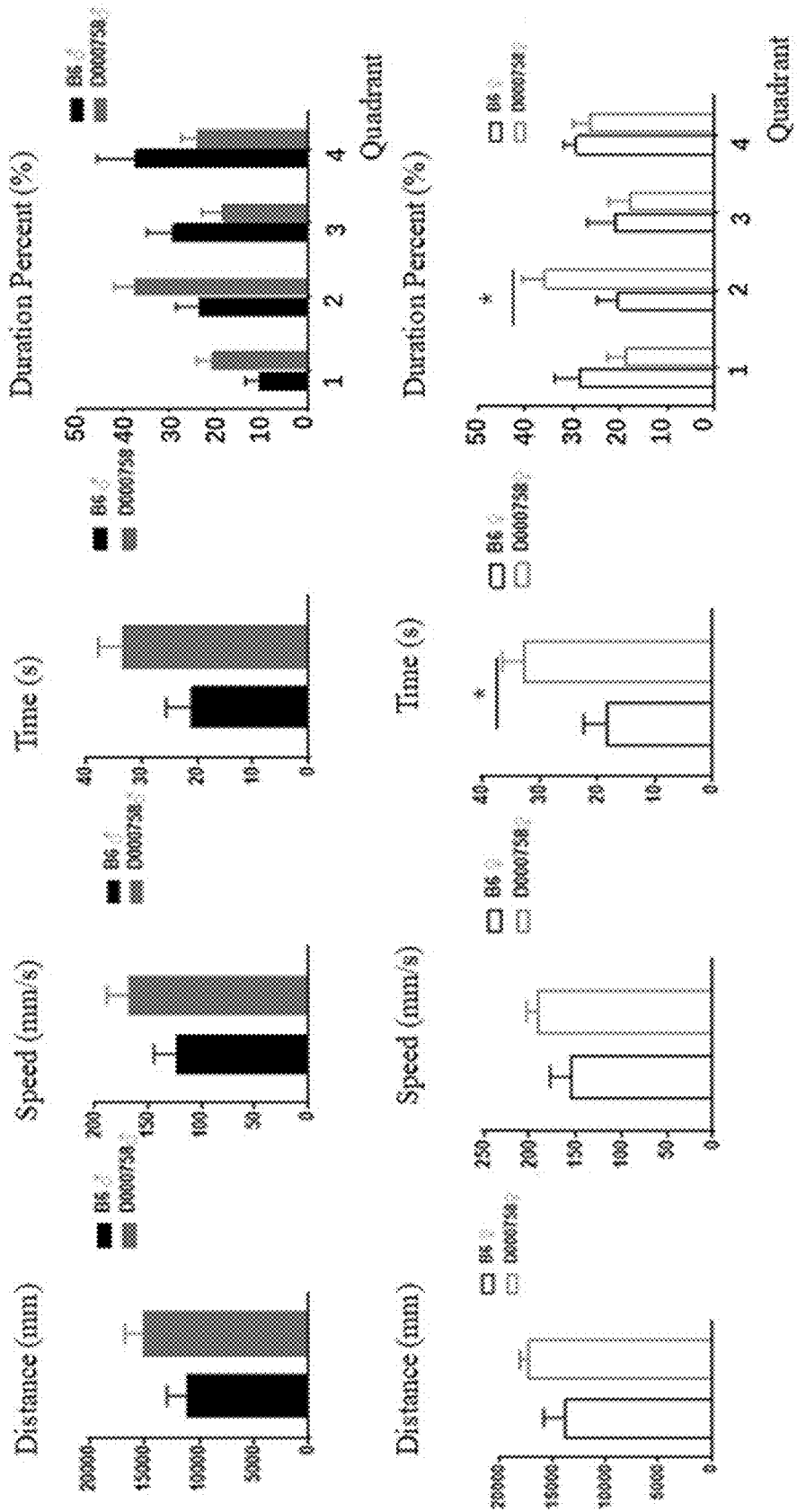
Figure 8:
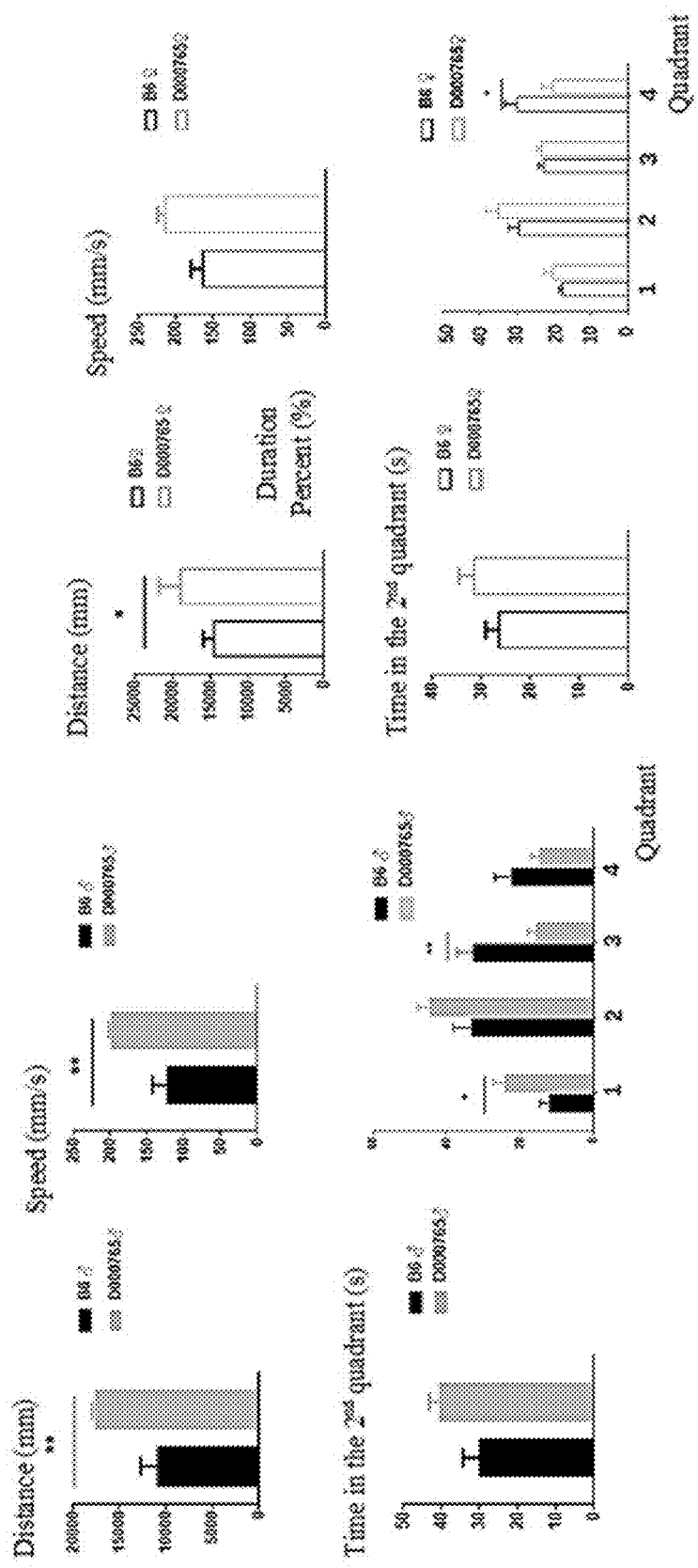

The test results are shown in FIG. 7 to FIG. 8. Of those, the results of the control mice (B6) are all on the left column of the bar graph. The results show that the distance, speed, time, and percent of the second quadrant of D0007586♂ are not significantly different from the control male mouse; and the time and the percent of the second quadrant of D000758 ♀ are significantly higher than those of the control female mouse. The distance and speed of D0007656♂ are significantly higher than those of the control male mouse; and the distance of D000765 ♀ is significantly higher than that of the control female mouse.

Example 5. Space Exploration Y Maze Test

Test Procedures:

On the test day, the mice were transferred to the test room and kept undisturbed for at least 30 min before the detection. The region III was closed. The mice were removed from the cage, and gently placed in the region I by making its head toward the region 0. The video recording software was run, and the record button was clicked simultaneously with timing. At the same time, the experimenter was kept away from the detection region, so that the mice could not see the experimenter.

The mice were allowed to explore freely in the other two regions for 3 min.

At the end of free exploration of mice, a memory test was performed at an interval of 2 hours.

Memory Test: All the regions were opened, and the mice were allowed to explore freely for 3 min.

The times of entering each region, the time length of exploration in each region, and the distances of the mice in the memory test were recorded.

When a clear M-mode map of left ventricle appeared, the Frame Store button was clicked to save at least 4 maps.

After the test of each mouse was finished, the excreta in the box should be removed, cleaned with 75% alcohol, and air dried. Then, the next mouse went to be tested.

Test Results:

The test results are shown in Tables 6A-6B:

TABLE 6A

Results of Space Exploration Y Maze Test

| Group | Animal Number. | New Arm Duration (s) | Distance (mm) | Number of Times |
|---|---|---|---|---|
| B6♂ | 643 | 44.80 | 1556.00 | 7 |
|  | 646 | 0.00 | 0.00 | 0 |
|  | 647 | 51.52 | 1349.22 | 5 |
|  | 648 | 24.12 | 797.29 | 4 |
|  | 649 | 48.24 | 1690.50 | 6 |
|  | 695 | 0.00 | 0.00 | 0 |
|  | 696 | 48.12 | 1952.81 | 9 |
|  | 697 | 46.28 | 1871.19 | 7 |
|  | 698 | 48.08 | 1591.55 | 6 |
|  | 699 | 38.64 | 1393.84 | 8 |
| Average value |  | 34.98 | 1220.24 | 5.2 |
| D000758 ♂ | 137 | 69.16 | 1297.89 | 4 |
|  | 138 | 30.92 | 704.30 | 1 |
|  | 139 | 88.44 | 2027.52 | 6 |
|  | 170 | 63.92 | 1071.20 | 3 |
|  | 171 | 68.60 | 1957.74 | 5 |
|  | 172 | 68.52 | 1844.91 | 5 |
|  | 173 | 72.96 | 1598.79 | 5 |
| Average value |  | 66.07428571 | 1500.335714 | 4.1 |
| P value (vs. B6 ♂) |  | 0.004149185 | 0.356319247 | 0.37834566 |

| Group | Animal Number. | New Arm Duration (s) | Distance (mm) | Number of Times |
|---|---|---|---|---|
| B6♀ | 620 | 67.00 | 1897.86 | 8 |
|  | 622 | 82.44 | 2629.04 | 9 |
|  | 623 | 61.04 | 2242.72 | 10 |
|  | 624 | 60.36 | 2367.87 | 9 |
|  | 644 | 62.72 | 2177.82 | 9 |
|  | 665 | 78.12 | 1438.70 | 4 |
|  | 666 | 54.56 | 1635.05 | 7 |
|  | 667 | 70.96 | 2746.50 | 10 |
|  | 668 | 131.16 | 1042.47 | 3 |
|  | 669 | 103.72 | 1896.53 | 5 |
| Average value |  | 77.208 | 2007.456 | 7.4 |
| D000758 ♀ | 156 | 60.16 | 1018.51 | 4 |
|  | 162 | 6.88 | 264.73 | 1 |
|  | 163 | 5.56 | 1009.59 | 2 |
|  | 164 | 95.64 | 1516.81 | 4 |
|  | 165 | 42.28 | 1534.89 | 5 |
|  | 166 | 34.44 | 1894.49 | 3 |
|  | 167 | 78.40 | 1000.39 | 2 |
| Average value |  | 46.19428571 | 1177.058571 | 3 |
| P value (vs. B6 ♀) |  | 0.064899153 | 0.00720447 | 0.000417684 |

TABLE 6B

Results of Space Exploration Y Maze Test

| Group | Animal Number. | Number of Times | Duration (s) | Distance (mm) | Group | Animal Number. | Number of Times | Duration (s) | Distance (mm) |
|---|---|---|---|---|---|---|---|---|---|
| B6♂ | 145 | 4 | 15.12 | 659.66 | B6♀ | 918 | 7 | 62.6 | 1962.73 |
|  | 146 | 4 | 25.36 | 1100.72 |  | 195 | 7 | 53.28 | 1712.53 |
|  | 147 | 6 | 47.96 | 1609.66 |  | 196 | 6 | 47.88 | 1482.16 |
|  | 148 | 4 | 30.72 | 1348.78 |  | 928 | 9 | 46.08 | 2298.59 |

TABLE 6B-continued

Results of Space Exploration Y Maze Test

| Group | Animal Number. | Number of Times | Duration (s) | Distance (mm) | Group | Animal Number. | Number of Times | Duration (s) | Distance (mm) |
|---|---|---|---|---|---|---|---|---|---|
| | 149 | 5 | 52.64 | 1538.7 | | 919 | 8 | 57.76 | 2725.51 |
| | 190 | 5 | 32.88 | 1109.1 | | 906 | 5 | 23.4 | 1063.8 |
| | 191 | 4 | 21.32 | 850.32 | | 907 | 7 | 54 | 1890.45 |
| | 192 | 5 | 30.52 | 1233.15 | | 908 | 6 | 41.12 | 1638.89 |
| | 193 | 6 | 33.44 | 1188.85 | | 909 | 5 | 32.96 | 1102.04 |
| | 194 | 7 | 47.32 | 1803.08 | | 929 | 12 | 85.84 | 3470.02 |
| Average value | | 5 | 33.728 | 1244.202 | Average value | | 7.2 | 50.492 | 1934.672 |
| D000765♂ | 900 | 2 | 35.16 | 568.48 | D000765♀ | 927 | 2 | 46.8 | 741.58 |
| | 910 | 4 | 66.84 | 1421.35 | | 924 | 2 | 25.6 | 777.86 |
| | 901 | 3 | 33.2 | 792.35 | | 925 | 4 | 50.16 | 1422.03 |
| | 902 | 3 | 43.96 | 1063.71 | | 926 | 5 | 39.44 | 1607.45 |
| | 903 | 2 | 36.4 | 823.35 | | 927 | 2 | 34.28 | 678.53 |
| | 904 | 0 | 0 | 0 | | 920 | 3 | 37.08 | 1063.89 |
| | 905 | 3 | 51.48 | 1128.92 | | 914 | 1 | 36.52 | 390.97 |
| | 911 | 2 | 14.72 | 499.37 | | 915 | 2 | 147 | 550.9 |
| | 912 | 2 | 20.2 | 506.25 | | 916 | 5 | 43.84 | 1433.19 |
| | 913 | 3 | 73.28 | 1103.56 | | 917 | 4 | 64.48 | 1372.4 |
| Average value | | 2.4 | 37.524 | 790.734 | Average value | | 3 | 52.52 | 1003.88 |
| P value (vs. B6 ♂) | | 0.000035 | 0.648247 | 0.016091 | P value (vs. B6 ♀) | | 0.00008 | 0.87116 | 0.00379 |

Figure 9:
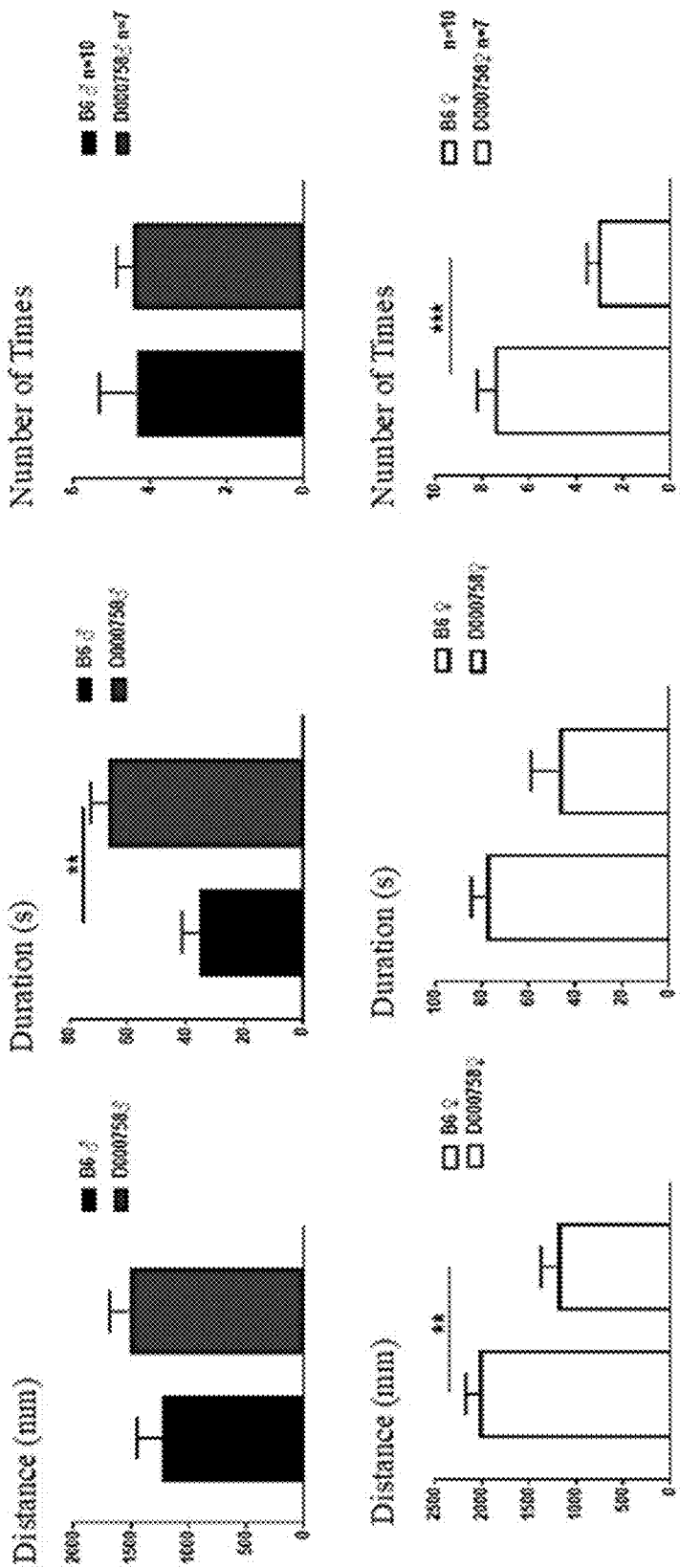
FIG. 9 to FIG. 10 show the results of the space exploration Y maze test of the mouse with high intelligence level of the present application.
Figure 10:
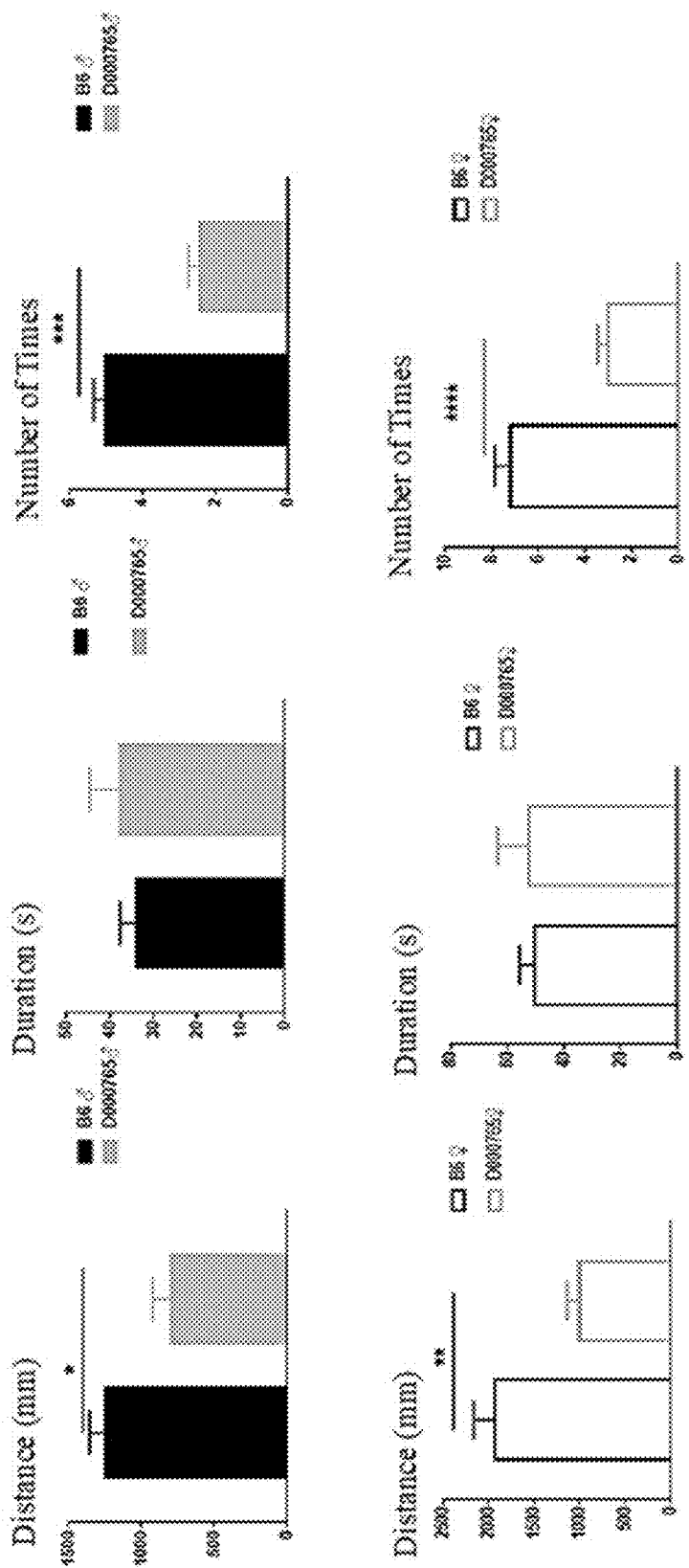

The test results are shown in FIG. 9 to FIG. 10. Of those, the results of the control mice (B6) are all on the left column of the bar graph. The results show that the duration of D000758 male mice was significantly higher than that of the control male mouse; and the distance and the number of times of D000758 female mouse were significantly less than those of the control female mouse. The distance and the number of times of D000765 male and female mice were significantly less than the control male and female mice.

Example 6. Active Avoidance Y Maze Test

Test Procedures:

The lower arm of the Y maze (Region I) was specified as the initiation region, the left arm (Region II) was specified as the safe region, the right arm (Region III) was specified as the shocking region, and the intersection of the three arms was the isolation region (Region 0).

On the test day, the mice were transferred to the test room and kept undisturbed for at least 30 min before the detection.

The test mice were placed into the maze to adapt for 5 min. Then, the mice were allowed to enter any arm of the maze.

The mice were subject to continuous circuit training test as follows: at the beginning of each training test, the animal was placed in the initiation region; the door of the initiation region was opened, and after 5 seconds, all the sites of the maze except the safe region were shocked with 2-second shocking once every 5 seconds. After entering the safe region, the mice were restricted within the target arm for 30 seconds. If the animal reached the safe region within 5 seconds from the opening of the door of the initiation region, it was considered as "correct".

The training was continued until a standard of 7 continuous "correction" was achieved. The training number when the standard was achieved was recorded on spot.

After the training was finished, the maze was cleaned with 70% alcohol solution, and the next mouse began to be trained.

After 24 hours, the mice were tested for 10 times with the same method. The number of times of avoidance errors, recognition errors, and total errors were counted. It is an avoidance error if the mouse failed to leave the initiation region within 5 seconds, and it is a recognition error if the mouse left the initiation region within 5 seconds, but entered the shocking region.

Test Results:

The test results are shown in Tables 7A-7B:

TABLE 7A

Results of Active Avoidance Y Maze Test

| Group | Animal Number. | Total Number of Times of Entering the Arms | Percent of Avoidance Error (%) | Percent of Recognition Error (%) | Percent of Accuracy (%) |
|---|---|---|---|---|---|
| B6♂ | 646 | 14 | 10 | 20 | 70 |
| | 647 | 10 | 10 | 50 | 40 |
| | 648 | 14 | 10 | 70 | 20 |
| | 649 | Learning Failure | 0 | 20 | 80 |
| | 643 | 7 | 10 | 0 | 90 |
| | 695 | 9 | 10 | 0 | 90 |
| | 696 | 14 | 0 | 100 | 0 |

TABLE 7A-continued

Results of Active Avoidance Y Maze Test

|  | 697 | 7 | 10 | 0 | 90 |
|---|---|---|---|---|---|
|  | 698 | 7 | 10 | 20 | 70 |
|  | 699 | 7 | 0 | 0 | 100 |
| Average value |  | 10 | 7 | 28 | 65 |
| D000758♂ | 170 | 9 | 0 | 20 | 80 |
|  | 171 | 10 | 0 | 30 | 70 |
|  | 172 | 20 | 0 | 50 | 50 |
|  | 173 | 7 | 0 | 0 | 100 |
|  | 137 | 7 | 0 | 0 | 100 |
|  | 138 | Learning Failure | 0 | 80 | 20 |
|  | 139 | 7 | 0 | 0 | 100 |
| Average value |  | 10 | 0 | 25.71428571 | 74.28571429 |
| P value (vs. B6 ♂) |  | 0.963225 | 0.00132 | 0.88760 | 0.56376 |

| Group | Animal Number | Total Number of Times of Entering the Arms | Percent of Avoidance (%) | Percent of Recognition Error (%) | Percent of Accuracy (%) |
|---|---|---|---|---|---|
| B6♀ | 620 | 12 | 20 | 10 | 70 |
|  | 622 | 7 | 10 | 50 | 40 |
|  | 623 | 7 | 30 | 10 | 60 |
|  | 624 | 7 | 10 | 60 | 40 |
|  | 644 | 18 | 10 | 30 | 60 |
|  | 665 | 18 | 0 | 40 | 60 |
|  | 666 | 22 | 40 | 50 | 40 |
|  | 667 | 19 | 0 | 30 | 70 |
|  | 668 | 7 | 0 | 0 | 100 |
|  | 669 | 12 | 10 | 40 | 50 |
| Average value |  | 13 | 13 | 32 | 59 |
| D000758♀ | 164 | 7 | 40 | 10 | 50 |
|  | 165 | 7 | 20 | 10 | 70 |
|  | 166 | Learning Failure | 80 | 10 | 0 |
|  | 167 | 13 | 0 | 0 | 100 |
|  | 156 | 7 | 0 | 10 | 90 |
|  | 162 | 7 | 0 | 50 | 50 |
|  | 163 | 7 | 10 | 50 | 40 |
| Average value |  | 8.00 | 21.43 | 20.00 | 57.14 |
| P value (vs. B6 ♀) |  | 0.0376 | 0.5027 | 0.2554 | 0.8972 |

TABLE 7B

Results of Active Avoidance Y Maze Test

| Group | Animal Number | Total Number of Times of Entering the Arms | Percent of Avoidance (%) | Percent of Recognition Error (%) | Percent of Accuracy (%) | Group | Animal Number | Total Number of Times of Entering the Arms | Percent of Avoidance (%) |
|---|---|---|---|---|---|---|---|---|---|
| B6♂ | 145 | 4 | 15.12 | 659.66 | | B6♀ | 918 | 7 | 62.6 | 1962.73 |
|  | 146 | 4 | 25.36 | 1100.72 | |  | 195 | 7 | 53.28 | 1712.53 |
|  | 147 | 6 | 47.96 | 1609.66 | |  | 196 | 6 | 47.88 | 1482.16 |
|  | 148 | 4 | 30.72 | 1348.78 | |  | 928 | 9 | 46.08 | 2298.59 |
|  | 149 | 5 | 52.64 | 1538.7 | |  | 919 | 8 | 57.76 | 2725.51 |
|  | 190 | 5 | 32.88 | 1109.1 | |  | 906 | 5 | 23.4 | 1063.8 |
|  | 191 | 4 | 21.32 | 850.32 | |  | 907 | 7 | 54 | 1890.45 |
|  | 192 | 5 | 30.52 | 1233.15 | |  | 908 | 6 | 41.12 | 1638.89 |
|  | 193 | 6 | 33.44 | 1188.85 | |  | 909 | 5 | 32.96 | 1102.04 |
|  | 194 | 7 | 47.32 | 1803.08 | |  | 929 | 12 | 85.84 | 3470.02 |
| Average value |  | 5 | 33.728 | 1244.202 | | Average value |  | 7.2 | 50.492 | 1934.672 |
| D000765♂ | 900 | 2 | 35.16 | 568.48 | | D000765♀ | 927 | 2 | 46.8 | 741.58 |
|  | 910 | 4 | 66.84 | 1421.35 | |  | 924 | 2 | 25.6 | 777.86 |
|  | 901 | 3 | 33.2 | 792.35 | |  | 925 | 4 | 50.16 | 1422.03 |
|  | 902 | 3 | 43.96 | 1063.71 | |  | 926 | 5 | 39.44 | 1607.45 |
|  | 903 | 2 | 36.4 | 823.35 | |  | 927 | 2 | 34.28 | 678.53 |
|  | 904 | 0 | 0 | 0 | |  | 920 | 3 | 37.08 | 1063.89 |
|  | 905 | 3 | 51.48 | 1128.92 | |  | 914 | 1 | 36.52 | 390.97 |

TABLE 7B-continued

Results of Active Avoidance Y Maze Test

| Group | Animal Number. | Total Number of Times of Entering the Arms | Percent of Avoidance (%) | Percent of Recognition Error (%) | Percent of Accuracy (%) | Group | Animal Number | Total Number of Times of Entering the Arms | Percent of Avoidance (%) |
|---|---|---|---|---|---|---|---|---|---|
| | 911 | 2 | 14.72 | 499.37 | | | 915 | 2 | 147 | 550.9 |
| | 912 | 2 | 20.2 | 506.25 | | | 916 | 5 | 43.84 | 1433.19 |
| | 913 | 3 | 73.28 | 1103.56 | | | 917 | 4 | 64.48 | 1372.4 |
| Average value | | 2.4 | 37.524 | 790.734 | | Average value | | 3 | 52.52 | 1003.88 |
| P value (vs. B6 ♂) | | 0.000035 | 0.648247 | 0.016091 | | P value (vs. B6 ♀) | | 0.00008 | 0.87116 | 0.00379 |

Figure 11:
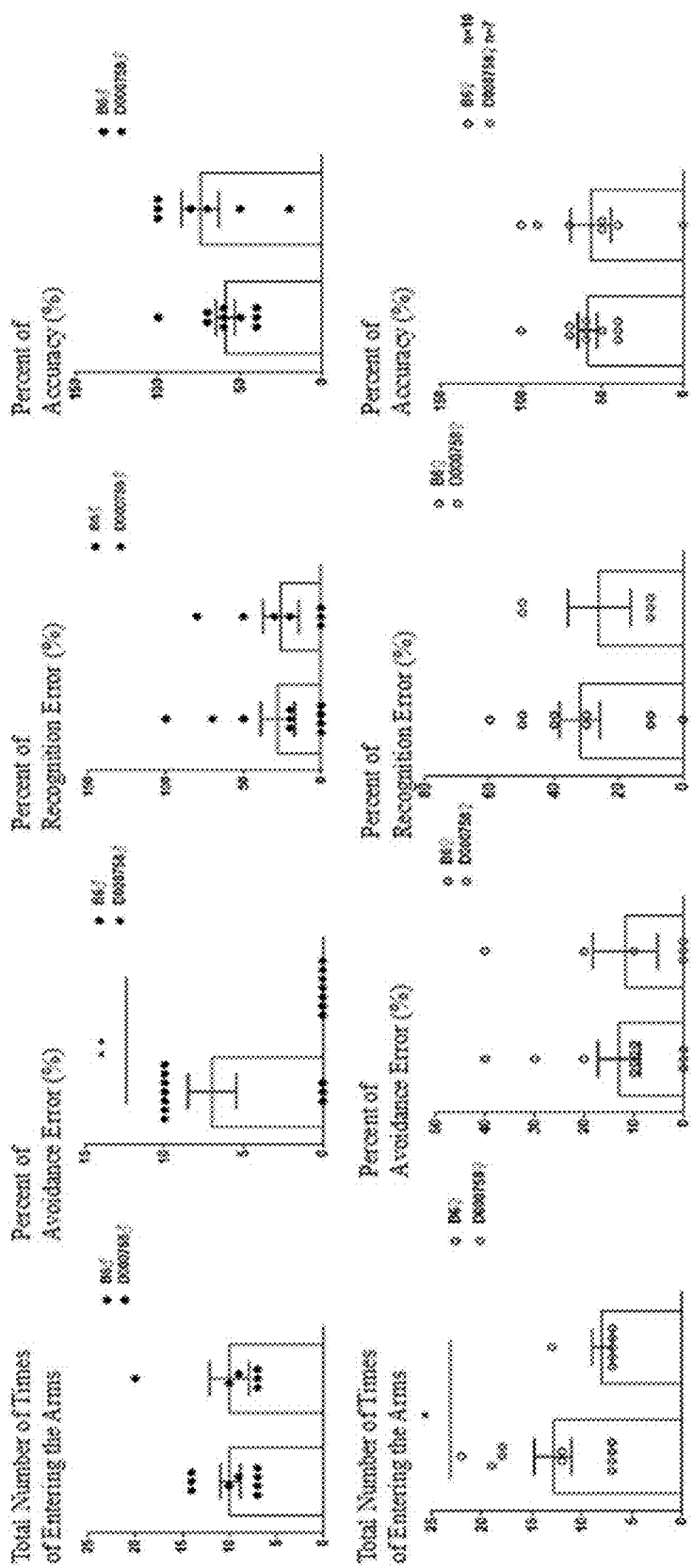
FIG. 11 to FIG. 12 show the results of the active avoid Y maze test of the mouse with high intelligence level of the present application.
Figure 12:
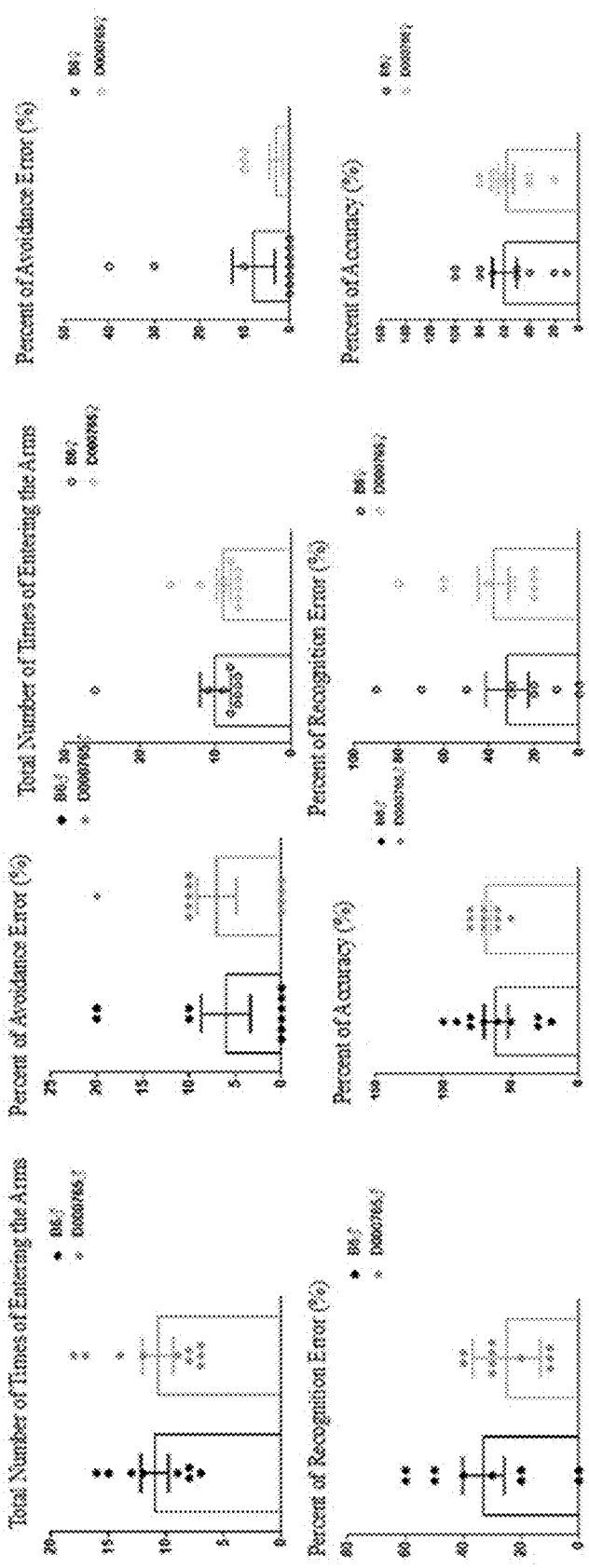

The test results are shown in FIG. 11 to FIG. 12. Of those, the results of the control mice (B6) are all on the left column of the bar graph. The results show that the percent of avoidance error of D000758 male mice was significantly less than that of the control male mouse; the percent of avoidance error of D000758 female mice was significantly less than that of the control female mouse. As for the percent of recognition error and the percent of accuracy, D000758 male and female mice do not exhibit a significant difference as compared with the control male and female mice. With respect to the total number of times of entering the arms, the percent of avoidance error, the percent of recognition error, and the percent of accuracy, D000765 male and female mice do not exhibit a significant difference as compared with the control male and female mice.

Example 7. Fatigue Rotarod Test

Test Procedures:

The experimental mice were to be adapted in the test room for 30 min before each experiment.

Training: the experimental mice should be trained for 3 consecutive days before the formal test with training for three times a day at an interval of 30 min to adapt the instrument. The mice were placed on the Rotarod System. 10 seconds later, the training speed was set at 1 rpm/min for 30 seconds, and then the speed was increased by 1 rpm until reaching 10 rpm/min every 30 seconds. At that time, the training was stopped after the speed is increased to 10 rpm/min.

Test:

a) The power supply was connected, and the switch of the instrument was turned on.

b) The speed was set at 0 rpm/min. The mice were placed onto the rotarod in accordance with the channel sequence. After the last mice was placed, the timer was started.

c) Starting from 0 rpm, the speed was increased by 1 rpm every 10 seconds.

d) During the test, the falling time of mice and the rotating speed of the rotarod at the falling were recorded.

e) The test instrument was cleaned, and the steps b to d were repeated twice after an interval of 30 min.

f) The average value of three falling time (s) and the rotating speeds of rotarod were taken as the test results of the days.

g) At the end of the test, the power of the instrument was turned off. The instrument was cleaned with 75% ethanol, and the desktop was tidied up.

Test Results:

The test results are shown in Tables 8A-8B:

TABLE 8A

Results of Fatigue Rotarod Test

| Group | Animal Number | First Time (s) | Second Time (s) | Third Time (s) | Average Value | Group | Animal Number | First Time (s) | Second Time (s) | Third Time (s) | Average Value |
|---|---|---|---|---|---|---|---|---|---|---|---|
| B6♂ | 647 | 217.2 | 233.2 | 312.3 | 254.2 | ♀ | 620 | 321.8 | 351.9 | 450.6 | 374.8 |
| | 648 | 226.2 | 232.7 | 165.2 | 208.0 | | 622 | 275.8 | 353.7 | 326.5 | 318.7 |
| | 649 | 238.5 | 186.4 | 220.2 | 215.0 | | 623 | 228.3 | 265.4 | 309.5 | 267.7 |
| | 643 | 232.1 | 211.4 | 263.8 | 235.8 | | 624 | 157.0 | 220.0 | 441.2 | 272.7 |
| | 695 | 151.2 | 284.0 | 161.4 | 198.9 | | 644 | 189.9 | 233.2 | 276.4 | 233.2 |
| | 696 | 237.6 | 333.2 | 206.3 | 259.0 | | 665 | 52.3 | 186.4 | 223.1 | 153.9 |
| | 697 | 241.4 | 171.4 | 233.7 | 215.5 | | 666 | 186.0 | 332.5 | 395.1 | 304.5 |
| | 698 | 155.7 | 219.3 | 338.4 | 237.8 | | 667 | 276.2 | 350.4 | 400.1 | 342.2 |
| | 699 | 92.5 | 199.1 | 238.4 | 176.7 | | 668 | 345.8 | 380.0 | 230.8 | 318.9 |
| D000758 ♂ | 170 | 60.8 | 79.5 | 80.9 | 73.7 | | 669 | 341.6 | 473.4 | 229.8 | 348.3 |
| | 171 | 138.6 | 156.2 | 128.7 | 141.2 | D000758 ♀ | 164 | 182.5 | 181.3 | 155.7 | 173.2 |
| | 172 | 26.5 | 39.7 | 40.5 | 35.6 | | 165 | 218.5 | 253.8 | 295.4 | 255.9 |
| | 173 | 121.4 | 100.4 | 106.8 | 109.5 | | 166 | 208.7 | 256.1 | 184.3 | 216.4 |
| | 137 | 94.5 | 102.4 | 171.4 | 122.8 | | 167 | 158.9 | 183.7 | 154.0 | 165.5 |
| | 138 | 180.3 | 148.3 | 211.9 | 180.2 | | 156 | 120.1 | 224.5 | 214.1 | 186.2 |
| | 139 | 61.6 | 74.8 | 73.4 | 69.9 | | 162 | 83.8 | 91.4 | 152.8 | 109.3 |
| P value (vs. B6 ♂) | | | | | 0.00031 | | 163 | 184.6 | 251.8 | 304.3 | 246.9 |
| | | | | | | P value (vs. B6 ♀) | | | | | 0.00290 |

TABLE 8B

Results of Fatigue Rotarod Test

| Group | Animal Number | First Time (s) | Second Time (s) | Third Time (s) | Average Value |
|---|---|---|---|---|---|
| B6♂ | 647 | 217.2 | 233.2 | 312.3 | 254.2 |
| | 648 | 226.2 | 232.7 | 165.2 | 208.0 |
| | 649 | 238.5 | 186.4 | 220.2 | 215.0 |
| | 643 | 232.1 | 211.4 | 263.8 | 235.8 |
| | 695 | 151.2 | 284.0 | 161.4 | 198.9 |
| | 696 | 237.6 | 333.2 | 206.3 | 259.0 |
| | 697 | 241.4 | 171.4 | 233.7 | 215.5 |
| | 698 | 155.7 | 219.3 | 338.4 | 237.8 |
| | 699 | 92.5 | 199.1 | 238.4 | 176.7 |
| ♂D000765 | 900 | 135.0 | 105.4 | 96.2 | 112.2 |
| | 910 | 82.0 | 99.5 | 108.3 | 96.6 |
| | 901 | 89.1 | 126.7 | 129.6 | 115.1 |
| | 902 | 251.3 | 319.9 | 292.1 | 287.8 |
| | 903 | 129.5 | 127.1 | 121.0 | 125.9 |
| | 904 | 144.7 | 88.9 | 135.4 | 123.0 |
| | 905 | 105.2 | 101.1 | 141.5 | 115.9 |
| | 911 | 140.5 | 165.5 | 148.0 | 151.3 |
| | 912 | 193.2 | 81.5 | 189.8 | 154.8 |
| | 913 | 161.4 | 122.9 | 114.4 | 132.9 |
| P value (vs. B6 ♂) | | | | | 0.00102 |
| B6♀ | 918 | 321.8 | 351.9 | 450.6 | 374.8 |
| | 195 | 275.8 | 353.7 | 326.5 | 318.7 |
| | 196 | 228.3 | 265.4 | 309.5 | 267.7 |
| | 928 | 157.0 | 220.0 | 441.2 | 272.7 |
| | 919 | 189.9 | 233.2 | 276.4 | 233.2 |
| | 906 | 52.3 | 186.4 | 223.1 | 153.9 |
| | 907 | 186.0 | 332.5 | 395.1 | 304.5 |
| | 908 | 276.2 | 350.4 | 400.1 | 342.2 |
| | 909 | 345.8 | 380.0 | 230.8 | 318.9 |
| | 929 | 341.6 | 473.4 | 229.8 | 348.3 |
| ♀D000765 | 923 | 174.6 | 219.8 | 264.8 | 219.7 |
| | 924 | 145.4 | 281.0 | 255.4 | 227.3 |
| | 925 | 129.8 | 203.0 | 254.4 | 195.7 |
| | 926 | 128.5 | 258.4 | 294.1 | 227.0 |
| | 927 | 209.1 | 195.6 | 357.9 | 254.2 |
| | 920 | 211.4 | 258.0 | 238.1 | 235.8 |
| | 914 | 121.9 | 92.3 | 232.2 | 148.8 |
| | 915 | 440.0 | 440.0 | 383.1 | 421.0 |
| | 916 | 272.1 | 243.0 | 326.1 | 280.4 |
| | 917 | 211.5 | 315.0 | 383.1 | 303.2 |
| P value (vs. B6 ♀) | | | | | 0.18945 |

Figure 13:
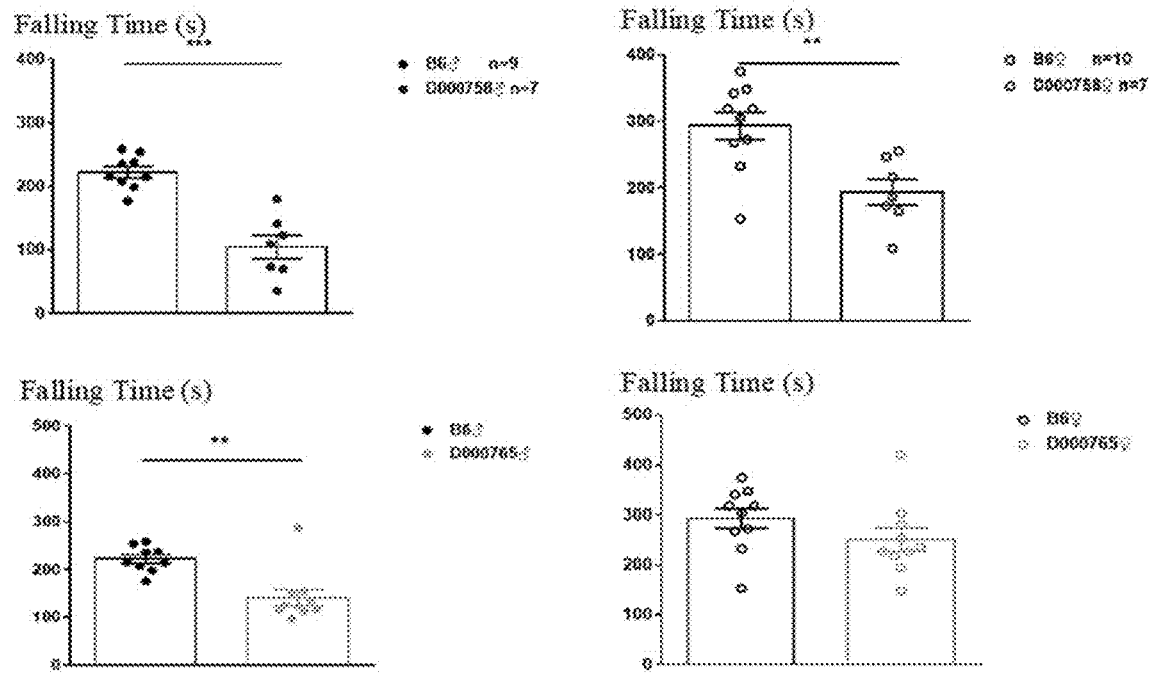
FIG. 13 shows the result of the fatigue rotarod test of the mouse with high intelligence level of the present application.

Test Results are shown in FIG. 13. Of those, the results of the control mice (B6) are all on the left column of the bar graph. The results show that the rotarod time of D000758 male and female mice is both significantly less than those of the control male and female mice. The rotarod time of D000765 male mice is all significantly less than the control male mouse.

Example 8. Measurement of Body Weight

Figure 14:
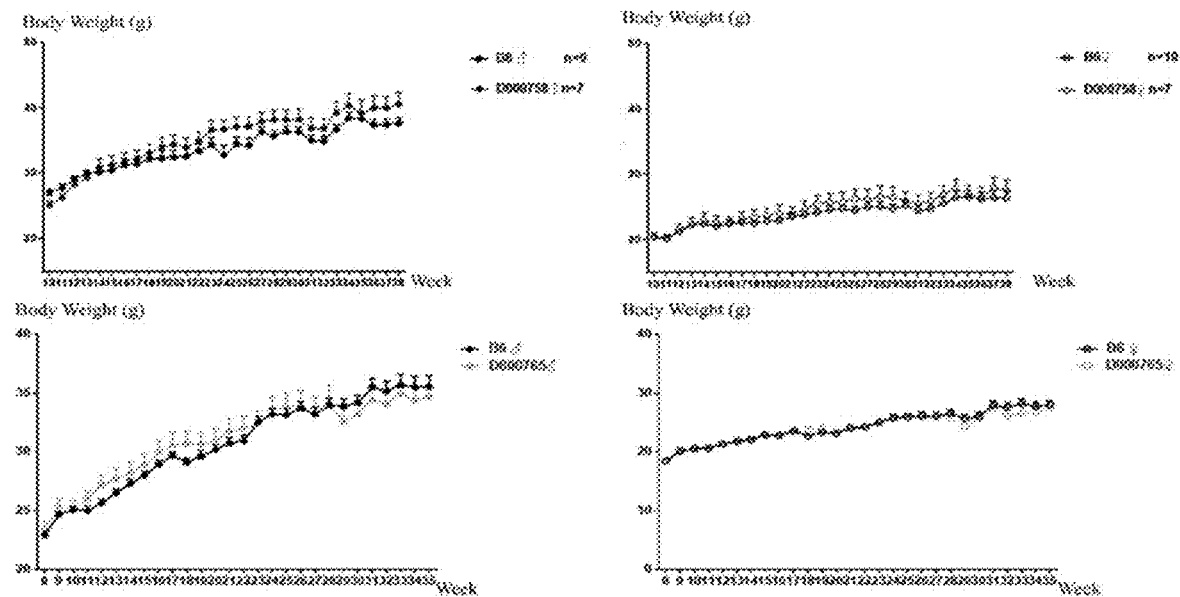
FIG. 14 shows the result of the body weight measurement of the mouse with high intelligence level of the present application.

Test Procedures:
The mice of Example 1 were weighed once per week.
Test Results:
Test results are shown in FIG. 14. The results show that there is no significant difference in body weight between 35W mice which are normally fed and subjected to endpoint sampling.

The aforesaid detailed descriptions are provided in an illustrative and exemplary manner, and are not intended to limit the scope of the appended claims. Various modifications of embodiments currently listed in the present application are apparent for persons skilled in the art, and encompassed within the scope of the appended claims and their equivalents.

What is claimed is:

1. A method for evaluating safety of a material using a D000765 mouse model, the method comprising:
    obtaining a resulting C57BL/6J mouse in which all or a portion of chromosome 1 is replaced by all or a portion of chromosome 1 from ZZ2 wild-type mouse;
    crossbreeding the resulting C57BL/6J mouse with C57BL/6J mouse in which chromosome 1 has not been replaced to produce a mouse in which chromosome 1 is heterozygous while the remainder chromosomes are homozygous;
    performing sibling selfing and screening by gene identification based on the mouse in which chromosome 1 is heterozygous while the remainder chromosomes are homozygous to obtain the D000765 mouse model, wherein the D000765 mouse model has increased learning ability, memory ability, and space exploration ability, when compared to a control wild-type C57BL/6J mouse;
    administering the material to the D000765 mouse model;
    determining whether the learning ability, memory ability, and space exploration ability of the D000765 mouse model is decreased after administration of the material, wherein a decrease in the learning ability, memory ability, and space exploration ability of the D000765 mouse model indicates that the material is not a safe material.

2. The method of claim 1, wherein the learning ability and/or memory ability are evaluated by a water maze test.

3. The method of claim 1, wherein the memory ability and/or space exploration ability are evaluated by a space exploration Y maze test.

4. The method of claim 1, wherein the memory ability is evaluated by an active avoidance Y maze test.

5. The method of claim 1, wherein the motor ability is evaluated by a fatigue rotarod test.

* * * * *